US010166351B2

(12) United States Patent
Eldredge et al.

(10) Patent No.: US 10,166,351 B2
(45) Date of Patent: Jan. 1, 2019

(54) ENHANCED SYSTEMS, PROCESSES AND APPARATUS FOR FACILITATING INTRANASAL TREATMENT OF A PATIENT AND PRODUCTS THEREBY

(75) Inventors: Stephen Eldredge, South Jordan, UT (US); Corey Ericksen, Fruit Heights, UT (US); Jeffrey O'Driscoll, Salt Lake City, UT (US); William Pipkin, Orem, UT (US)

(73) Assignee: Dolor Technologies, LLC, Syracuse, UT (US)

( * ) Notice: Subject to any disclaimer, the term of this patent is extended or adjusted under 35 U.S.C. 154(b) by 0 days.

(21) Appl. No.: 13/371,288

(22) Filed: Feb. 10, 2012

(65) Prior Publication Data

US 2012/0157968 A1 Jun. 21, 2012

Related U.S. Application Data

(63) Continuation-in-part of application No. 12/553,953, filed on Sep. 3, 2009.
(Continued)

(51) Int. Cl.
*A61B 17/24* (2006.01)
*A61M 25/00* (2006.01)
(Continued)

(52) U.S. Cl.
CPC .............. *A61M 15/08* (2013.01); *A61B 17/24* (2013.01); *A61M 11/007* (2014.02);
(Continued)

(58) Field of Classification Search
CPC .... A61M 15/08; A61M 15/085; A61M 11/00; A61M 11/007; A61M 11/06;
(Continued)

(56) References Cited

U.S. PATENT DOCUMENTS 3,856,009 A * 12/1974 Winnie .............. A61B 17/3401
604/170.03
4,588,398 A * 5/1986 Daugherty ........ A61M 25/0606
604/164.01
(Continued)

FOREIGN PATENT DOCUMENTS

WO 2009124192 10/2009

OTHER PUBLICATIONS

MedLink, Inc., "Your Journey to Migraine Relief Ends Here!" patient education video as published at https://www.treatmymigrainenow.com/index.php?/what-is-the-migrainator/.
(Continued)

*Primary Examiner* — Jenna Zhang
(74) *Attorney, Agent, or Firm* — Lowenstein Sandler LLP

(57) ABSTRACT

Systems are disclosed for facilitating intranasal treatment of a patient's sphenopalatine/pterygopalatine recess. Likewise the instant system is effective for addressing acute pain conditions, and is refined enough to be performed by physician's assistants, nurses, and other well-trained practitioners. Apparatus involved includes a sheath hub, a catheter hub, an arresting element, and an engagement element in embodiments. Engagement between the arresting element and the engagement element prevents rotation of the sheath hub with respect to the catheter hub.

12 Claims, 13 Drawing Sheets

Related U.S. Application Data

(60) Provisional application No. 61/094,323, filed on Sep. 4, 2008.

(51) Int. Cl.

| | | |
|---|---|---|
| *A61M 15/08* | (2006.01) | |
| *A61M 11/00* | (2006.01) | |
| *A61M 31/00* | (2006.01) | |
| *A61M 11/06* | (2006.01) | |
| *A61M 25/06* | (2006.01) | |

(52) U.S. Cl.
CPC ......... *A61M 25/0021* (2013.01); *A61M 11/06* (2013.01); *A61M 25/0032* (2013.01); *A61M 25/0041* (2013.01); *A61M 25/0071* (2013.01); *A61M 31/00* (2013.01); *A61M 2025/0004* (2013.01); *A61M 2025/0008* (2013.01); *A61M 2025/0681* (2013.01)

(58) Field of Classification Search
CPC .......... A61M 25/0032; A61M 25/0041; A61M 25/007; A61M 31/00; A61M 2210/0618; A61M 2025/0681; A61M 2025/0008; A61M 2025/0004
USPC .................................................. 604/514, 528
See application file for complete search history.

(56) References Cited

U.S. PATENT DOCUMENTS

| | | | |
|---|---|---|---|
| 4,886,493 A * | 12/1989 | Yee ..................... A61M 11/00 | 604/516 |
| 4,950,257 A * | 8/1990 | Hibbs ............... A61M 25/0069 | 604/167.02 |
| 5,405,323 A * | 4/1995 | Rogers ................. A61M 39/26 | 604/167.04 |
| 5,817,073 A | 10/1998 | Krespi | |
| 5,830,189 A | 11/1998 | Chang | |
| 5,879,333 A * | 3/1999 | Smith ............... A61M 25/0014 | 604/164.04 |
| 6,113,579 A * | 9/2000 | Eidenschink ..... A61M 25/0068 | 604/264 |
| 6,322,542 B1 | 11/2001 | Nilson et al. | |
| 6,322,548 B1 | 11/2001 | Payne et al. | |
| 6,350,465 B1 | 2/2002 | Jonnalagadda et al. | |
| 6,432,986 B2 | 8/2002 | Levin | |
| 6,491,940 B1 | 12/2002 | Levin | |
| 6,537,265 B2 | 3/2003 | Thanvala et al. | |
| 6,853,858 B2 | 2/2005 | Shalev | |
| 7,120,489 B2 | 10/2006 | Shalev et al. | |
| 7,632,243 B2 | 12/2009 | Bialecki et al. | |
| 2002/0095203 A1 * | 7/2002 | Thompson ............... A61F 2/95 | 623/1.11 |
| 2004/0015068 A1 | 1/2004 | Shalev et al. | |
| 2005/0072430 A1 | 4/2005 | Djupesland | |
| 2005/0281751 A1 | 12/2005 | Levin | |
| 2006/0106348 A1 * | 5/2006 | Lichtenberg ...... A61M 25/0637 | 604/164.08 |
| 2006/0167417 A1 * | 7/2006 | Kratz ................ A61M 25/0668 | 604/164.05 |
| 2006/0195169 A1 | 8/2006 | Gross et al. | |
| 2006/0287677 A1 | 12/2006 | Shalev et al. | |
| 2007/0021648 A1 | 1/2007 | Lenker et al. | |
| 2007/0083245 A1 | 4/2007 | Lamensdorf et al. | |
| 2007/0149979 A1 * | 6/2007 | Chana .................. A61B 17/175 | 606/96 |
| 2008/0279895 A1 | 6/2008 | Blumenfeld | |
| 2008/0172033 A1 | 7/2008 | Keith et al. | |
| 2008/0255542 A1 * | 10/2008 | Nimgaard ................ A61F 2/95 | 604/535 |
| 2009/0131867 A1 * | 5/2009 | Liu ..................... A61B 17/8811 | 604/96.01 |
| 2009/0259126 A1 * | 10/2009 | Saal .................... A61B 17/3401 | 600/433 |
| 2010/0010295 A1 * | 1/2010 | Sato ........................ A61B 1/018 | 600/104 |
| 2010/0030187 A1 | 2/2010 | Xia | |
| 2010/0030188 A1 | 2/2010 | Xia | |
| 2010/0057048 A1 | 3/2010 | Eldredge | |
| 2011/0104061 A1 | 5/2011 | Seward | |
| 2011/0152838 A1 * | 6/2011 | Xia ........................ A61M 11/06 | 604/514 |
| 2012/0017893 A1 | 1/2012 | Xia | |
| 2012/0053523 A1 * | 3/2012 | Harding ............ A61M 25/0618 | 604/164.08 |
| 2013/0030369 A1 * | 1/2013 | Root ................. A61M 25/0023 | 604/164.03 |
| 2013/0123705 A1 * | 5/2013 | Holm ................ A61M 25/0105 | 604/171 |
| 2014/0371598 A1 * | 12/2014 | Okubo ..................... A61B 8/12 | 600/467 |

OTHER PUBLICATIONS

Headache Control Clinic, "Headache Treatments: Sphenopaltine Ganglion Block" as published at http://www.headachecontrolclinic.com/spgblock.html.

Australian Patent Examination Report issued in Australian Patent Application No. 2012369170, dated Oct. 30, 2014.

* cited by examiner

ENHANCED SYSTEMS, PROCESSES AND APPARATUS FOR FACILITATING INTRANASAL TREATMENT OF A PATIENT AND PRODUCTS THEREBY

CROSS-REFERENCE TO RELATED APPLICATION

This application is a continuation-in-part of U.S. patent application Ser. No. 12/553,953 filed on Sep. 3, 2009, which claims the benefit of U.S. Provisional Application 61/094,323 filed on Sep. 4, 2008. The entire disclosures of application Ser. Nos. 12/553,953 and 61/094,323 are incorporated herein by reference, as if fully set forth herein.

FIELD OF ART

This subject matter relates to autonomic and nociceptive nerve blockade and more particularly relates to blockade of sphenopalatine/pterygopalatine ganglia. Specifically, the instant subject matter renders such treatment accessible to larger segments of the treatment-needing populace, owing in part to broadening the effective user base of the same from physicians only to qualified and trained medical professionals.

BACKGROUND OF THE ART

Autonomic pain is a type of nerve pain that arises due to abnormalities in the function of the autonomic nervous system. With autonomic pain, an abnormality in a group of nerves called a ganglion causes pain to an organ or body region. To treat autonomic-mediated pain physicians can block a ganglion with the injection or application of medication to a specific area of the body. To therapeutically treat acute pain a physician injects or applies a local anesthetic to the affected neuronal ganglion. This type of treatment may be referred to as a nerve block.

In 1908 Greenfield Sluder M D, published his article, "The role of the sphenopalitine ganglion in nasal headaches," in the *New York Medical Journal*. He advocated using a long needle through the side of the face to inject cocaine into the sphenopalatine ganglion (SPG) to treat certain severe recurrent headaches. More than a century of medical science has validated Sluder's basic premise: that sphenopalitine ganglion blockade (SPGB) is a valuable tool in headache management.

The SPG is a collection of nerve cells resting just beneath the thin tissues that line the back of the nasal passage. Because of the neural connections that pass through it, the SPG plays an essential role in various types of headaches. Temporary interruption of impulse conduction through the SPG can often abort headaches and sometimes provide long-term relief to headache sufferers.

Other conditions shown to respond to SPGB in published literature include: trigeminal neuralgia, dental pain, postpartum neck and back pain, complex regional pain syndrome, herpes zoster (Shingles), tempromandibular joint (TMJ) pain and primary hyperhydrosis.

Aside from the personal pain suffered by those who experience recurrent severe headaches, the staggering financial cost to society is difficult to estimate or comprehend. Just for the 30 million migraine sufferers in the United States, annual direct medical costs are estimated to exceed $12B, with lost productivity costing employers an additional $12B. Those figures do not include the rest of the world or the two dozen other types of cephalgia found in the World Health Organization's headache classification scheme.

An estimated 4-5% of the population suffers from chronic daily headaches which, by definition, impact a person's ability to function for at least 15 days a month for at least 3 months. Of those patients, 30% are managed with relatively inexpensive medications; 17% require pharmacologic regimens exceeding $500/month; and more than half continue to suffer a virtual failure of modern medicine.

Any intervention that reduces the incidence or duration of headaches has the potential to dramatically reduce personal suffering and to save patients, insurance companies and governments enormous sums of money. The SphenoCath™ brand of catheter system offers a simple, safe, inexpensive intervention, as explained herein and claimed below.

The SPG/pterygopalatine ganglia is a neuronal structure located principally in the center of the head in the pterygopalatine fossa posterior to the middle turbinate. The sphenopalatine/pterygopalatine ganglia comprises the largest cluster of sympathetic neurons in the head outside of the brain. The sphenopalatine/pterygopalatine ganglia interfaces and directs nerve impulses to the majority of the head's autonomic or parasympathetic pathways. Therefore, any abnormality or injury to this structure may cause severe pain. A nerve block of the sphenopalatine/pterygopalatine ganglia may relieve a variety of painful conditions ranging from headache to lower back pain. Additionally, other disease processes such as headache disorders and other neurological conditions can be arrested, or improved by local anesthetic blockade, and/or other pharmacological augmentation or mechanical alteration of the sphenopalatine/pterygopalatine ganglia and surrounding structures.

Unfortunately, because of the anatomical position of the SPG/pterygopalatine ganglia, the structure is very difficult to block with a local anesthetic solution. The anatomical location of the sphenopalatine/pterygopalatine ganglia is dangerously close to many vital and delicate mid brain structures. Although direct needle placement can be employed under fluoroscopic guidance to administer anesthetic to the sphenopalatine/pterygopalatine ganglia, most practitioners will not attempt the procedure due to the technical difficulty and extreme dangers of an aberrant needle placement.

Accessing the SPG/pterygopalatine recess to treat the SPG/pterygopalatine ganglia with a conventional device is difficult in that a conventional devices typically do not include a curvature for accessing the sphenopalatine/pterygopalatine recess. Further, even if a conventional needle were curved to access the sphenopalatine/pterygopalatine recess, once the curved needle were inserted into the patient's nasal cavity, the physician or other medical professional would not be able to identify the direction of the curve of the needle. Without fluoroscopic guidance, an insertion end of the needle may contact and/or damage the vital and delicate mid brain structures. To date, this limitation has limited both service-providers and patients from being involved to a large extent.

SUMMARY

From the foregoing discussion, it should be apparent that a need exists for a step change, namely an apparatus, system, and method for facilitating intranasal treatment on a patient which can be done safely, in due course, by those other than the top half-dozen medical professionals who can do so successfully. Beneficially, such an apparatus, system, and method would administer medication directly to the sphenopalatine/pterygopalatine ganglia.

The present subject matter has been developed in response to the present state of the art, and in particular, in response to the problems and needs in the art that have not yet been fully solved by currently available intranasal treatment apparatus, systems, and methods. Accordingly, the present subject matter has been developed to provide an apparatus, system, and method for intranasal treatment on a patient that overcome many or all of the above-discussed shortcomings in the art.

The apparatus to facilitate intranasal treatment of a patient's sphenopalatine/pterygopalatine recess includes, in certain embodiments, a sheath hub, a catheter hub, an arresting element, and an engagement element. The sheath hub has an exterior surface opposing an interior surface. The interior surface defines a catheter hub receiving space. The catheter hub is slideably received within the catheter hub receiving space and is positionable along a longitudinal axis of the sheath hub. The arresting element is positioned on one of the catheter hub and the sheath hub and the engagement element is positioned on the other of the catheter hub and the sheath hub. The arresting element continuously engages the engagement element when the catheter hub is positioned along the longitudinal axis of the sheath hub. Engagement between the arresting element and the engagement element prevents rotation of the sheath hub with respect to the catheter hub.

The apparatus, in one embodiment, includes a catheter and a rotational orientation indicator. The catheter is coupled to the catheter hub and at least a portion of the catheter includes an intrinsic curvature. The rotational orientation indicator identifies the rotational orientation of the intrinsic curvature of the catheter. In certain embodiments, the rotational orientation indicator comprises a raised ridge extending longitudinally along at least one of the sheath hub and the catheter hub. In other embodiments, the rotational orientation indicator only provides a visual indication of the rotational orientation of the intrinsic curvature of the catheter.

According to embodiments, the catheter includes an insertion end and a coupling end. In such an embodiment, the insertion end may include the intrinsic curvature with respect to a longitudinal axis of the catheter and the rotational orientation indicator identifies the rotational orientation of the intrinsic curvature of the catheter.

In certain embodiments, the apparatus includes a sheath coupled to the sheath hub and a catheter coupled to the catheter hub and received within the sheath. The catheter includes an insertion end and a coupling end with the insertion end having an intrinsic curvature with respect to a longitudinal axis of the catheter. In such an embodiment, the catheter hub is positionable between an inserted position and an extended position. With the catheter hub positioned in the extended position, the sheath straightens the intrinsic curvature of the catheter.

The catheter, in some embodiments, includes an insertion end having a tip that is curved such that the tip is rounded. The sheath includes an introduction end having an outermost edge that is sloped to a vertex. In such an embodiment, when the catheter hub is positioned in the extended position, the vertex aligns with a beginning of the curve of the rounded tip of the catheter. In certain embodiments, a transition between the vertex and the beginning of the curve of the rounded tip of the catheter is continuous when the catheter hub is positioned in the extended position. In one embodiment, a tip of the insertion end of the catheter is bulbous.

The arresting element, in certain embodiments, is a flange coupled to and extending perpendicularly from either an outer surface of the catheter hub or an interior surface of the sheath hub. In such an embodiment, the engagement element is a recess extending longitudinally along the other of the interior surface of the sheath hub or the outer surface of the catheter hub. The flange is positioned within and travels along the recess when the catheter hub is repositioned along the longitudinal axis of the sheath hub.

In certain embodiments, the apparatus includes a stopping element coupled to either the catheter hub or the sheath hub. The stopping element is configured to engage the arresting element to stop the catheter hub from being removed from the catheter hub receiving space. In one embodiment, the stopping element is configured to align the vertex of the sheath with the beginning of the curve of the rounded tip of the catheter when the catheter hub is positioned in the extended position.

In certain embodiments, the apparatus includes a sheath hub, a catheter hub, an arresting element, an engagement element, and a rotational orientation indicator. The sheath hub has an exterior surface opposing an interior surface. The interior surface defines a catheter hub receiving space. The catheter hub is slideably received within the catheter hub receiving space and is positionable along a longitudinal axis of the sheath hub. The arresting element is coupled to or positioned on either the catheter hub or the sheath hub. The engagement element is coupled to or positioned one or in the other of the catheter hub and the sheath hub. The arresting element continuously engages the engagement element when the catheter hub is repositioned along the longitudinal axis of the sheath hub. Engagement between the arresting element and the engagement element prevents rotation of the sheath hub with respect to the catheter hub. The rotational orientation indicator identifies a rotational orientation of at least one of the sheath hub and the catheter hub.

In certain embodiments, the rotational orientation indicator is a raised ridge extending longitudinally along at least one of the sheath hub and the catheter hub. The raised ridge identifies the rotational orientation of at least one of the sheath hub and the catheter hub both visually and tactilely.

According to embodiments, the apparatus includes a catheter coupled to the catheter hub. The catheter has an insertion end and a coupling end, with the insertion end having an intrinsic curvature with respect to a longitudinal axis of the catheter. In such an embodiment, the rotational orientation indicator identifies an orientation of the intrinsic curvature of the catheter.

The arresting element, in certain embodiments, includes a flange coupled to and extending perpendicularly from either an outer surface of the catheter hub or an interior surface of the sheath hub. In such an embodiment, the engagement element includes a recess extending longitudinally along the other of the interior surface of the sheath hub and the outer surface of the catheter hub. The flange of the arresting element is positioned within and travels along the recess of the engagement element when the catheter hub is repositioned along the longitudinal axis of the sheath hub.

In certain embodiments, the apparatus further includes a sheath coupled to the sheath hub and the catheter hub is positionable between an inserted position and an extended position. In the extended position, the sheath straightens the intrinsic curvature of the catheter. In one embodiment, a tip of the insertion end of the catheter is curved such that the tip is rounded. In such an embodiment, the sheath includes an introduction end and a connected end. An outermost edge of the introduction end is sloped to a vertex and the vertex aligns with a beginning of the curve of the rounded tip of the catheter when the catheter hub is repositioned within the sheath hub to the extended position.

An apparatus for facilitating intranasal treatment of a patient's sphenopalatine/pterygopalatine recess is also disclosed which includes a sheath hub, a catheter hub, an arresting element, an engagement element, a sheath, and a catheter. The sheath hub has an exterior surface opposing an interior surface. The interior surface defines a catheter hub receiving space and the catheter hub is slideably received within the catheter hub receiving space. The catheter hub is positionable along a longitudinal axis of the sheath hub. The arresting element is positioned on either the catheter hub or the sheath hub. The engagement element is positioned on or in the other of the catheter hub or the sheath hub. The arresting element continuously engages the engagement element when the catheter hub is repositioned along the longitudinal axis of the sheath hub between an inserted position and an extended position. The sheath is coupled to the sheath hub and includes an introduction end having an outermost edge. The catheter is received within the sheath and is coupled to the catheter hub. The catheter includes an insertion end having a tip that is curved such that the tip is rounded. The outermost edge of the sheath aligns with a beginning of the curve of the rounded tip of the catheter when the catheter hub is positioned in the extended position.

In certain embodiments, the outermost edge of the introduction end of the sheath is sloped to a vertex. In such an embodiment, the vertex aligns with the beginning of the curve of the rounded tip of the catheter when the catheter is positioned in the extended position. In one embodiment, a transition between the vertex and the beginning of the curve of the rounded tip of the catheter is continuous when the catheter hub is positioned in the extended position. In another embodiment, the tip of the insertion end of the catheter is bulbous. In such an embodiment, the bulbous tip of the insertion end of the catheter may shield the sheath to prevent the sheath from snagging delicate tissues within the patient's nasal cavity.

According to embodiments, there is disclosed process for addressing acute pain conditions timely, which comprises, in combination: providing an improved system comprising a removable tool defined by a sheath hub, a catheter hub, an arresting element and an engagement element, advancing the system into anatomically constrained spaces with a patient's nasal cavity, positioning the system whereby it is disposed adjacent at least a target tissue site within the sphenopalatine/ptergoplatine recess, and delivering at least one medical treatment selected from the group consisting of pharmaceutical, biologic, electrical/electronic stimulatory, sonic, mechanical and otherwise consisting essentially of pulsed or streamed energy to the at least a target tissue site.

According to embodiments, there is disclosed a kit, including directions for use and improved systems disclosed herein and claimed below.

Reference throughout this specification to features, advantages, or similar language does not imply that all of the features and advantages that may be realized with the present subject matter should be or are in any single embodiment of the subject matter. Rather, language referring to the features and advantages is understood to mean that a specific feature, advantage, or characteristic described in connection with an embodiment is included in at least one embodiment of the present subject matter. Thus, discussion of the features and advantages, and similar language, throughout this specification may, but do not necessarily, refer to the same embodiment.

Furthermore, the described features, advantages, and characteristics of the subject matter may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments of the subject matter.

These features and advantages of the present subject matter will become more fully apparent from the following description and appended claims, or may be learned by the practice of the subject matter as set forth hereinafter.

BRIEF DESCRIPTION OF THE DRAWINGS

In order that the advantages of the subject matter will be readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the accompanying drawings, in which.

DETAILED DESCRIPTION

The present inventors have discovered that enhanced systems can enable those who are not licensed physicians (non-surgically trained operators with training by licensed healthcare professionals) to address SPG issues with unexpected rates of success. While it is sometimes still approached with a needle through the side of the face, the SPG is now more often accessed through the nasal cavity. For decades, the standard approach through the nose utilized a rigid cotton-tipped applicator soaked with local anesthetic. This is particularly problematic when one recognizes that the path to the SPG is far from straight. Both the needle and the cotton-tipped applicator require considerable skill and training for the practitioner and pose potential risk and discomfort for the patient. Sometimes these approaches also require fluoroscopic guidance and/or sedation.

Other approaches to SPGB include a transoral approach, an endoscopic-assisted approach, dripping or aerosolizing medication into the nose or simply irrigating the area and assuming the medication will saturate the appropriate spot. Still others have advocated permanent disruption of the SPG by chemical, surgical, thermal or radio frequency ablation.

None of these approaches provides an office-based practitioner with a safe, simple, quick, precise method for consistently targeting the SPG. The SphenoCath™ brand of medical device, when used as designed, allows any practitioner the directional control necessary to deliver an appropriate dose of medication safely and painlessly to the SPG in an office setting without needles, sedation or narcotics.

Reference throughout this specification to "one embodiment," "an embodiment," or similar language means that a particular feature, structure, or characteristic described in connection with the embodiment is included in at least one embodiment of the present subject matter. Thus, appearances of the phrases "in one embodiment," "in an embodiment," and similar language throughout this specification may, but do not necessarily, all refer to the same embodiment.

Furthermore, the described features, structures, or characteristics of the subject matter may be combined in any suitable manner in one or more embodiments. In the following description, numerous specific details are provided for a thorough understanding of embodiments of the subject matter. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the subject matter.

Figure 1:
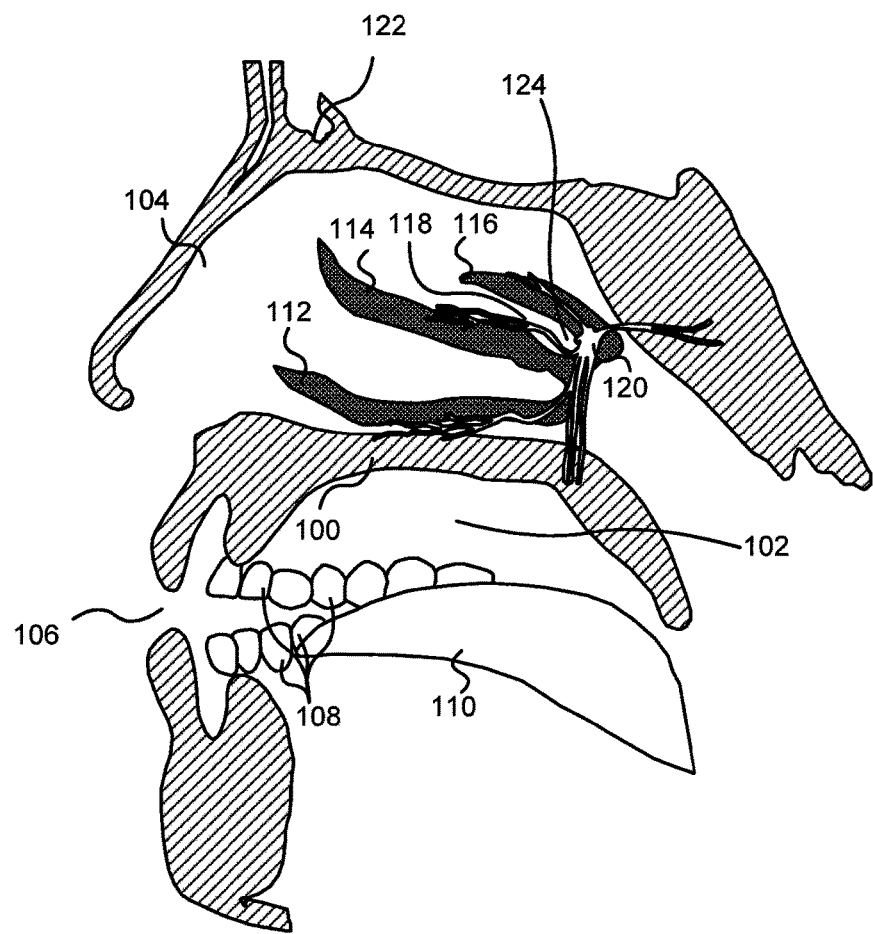
FIG. 1 is a cutaway view illustrating one embodiment of the facial anatomy of a patient upon which the apparatus, system and method of the present invention may be employed.

FIG. 1 is an illustration of one environment in which the present subject matter may be practiced. In particular, FIG. 1 depicts a cutaway view of the anatomical features of a typical human nasal cavity. One skilled in the art will recognize that certain anatomical features and structures of the human nasal cavity have been omitted to avoid obscuring the structures relevant to the practice of the current subject matter. To help orient the reader, the mouth 106 is illustrated with teeth 108 and tongue 110. The anatomical structures relevant to one practice of the current subject matter include the palate 100 which separates the oral cavity 102 from the nasal cavity 104, the inferior sinus turbinate 112, the middle sinus turbinate 114 and the superior sinus turbinate 116 as well as the nasal bone 122. The middle sinus turbinate 114 and superior sinus turbinate 116 define the sphenopalatine/pterygopalatine recess 118. Deep within the sphenopalatine/pterygopalatine recess 118 at the posterior 124 of the sphenopalatine/pterygopalatine recess 118 lies the sphenopalatine/pterygopalatine ganglia 120.

One skilled in the art will recognize that the medical community is not uniform in the terminology with regard to the sphenopalatine or pterygopalatine ganglia. Certain practitioners use sphenopalatine while others use pterygopalatine. Therefore, the present description will refer to the ganglion labeled 120 as the sphenopalatine/pterygopalatine ganglia 120. Similarly, the recess labeled 118 will be referred to as the sphenopalatine/pterygopalatine recess 118. However, this terminology is in no way limiting on the structure for which the present subject matter is intended. Where practitioners or scientist differentiate between the sphenopalatine ganglion or the pterygopalatine ganglia, the present disclosure will be understood to apply to either structure.

Autonomic pain is a type of nerve pain that arises due to abnormalities in the function of the autonomic nervous system. The majority of the "treatment resistant" headache population in the world suffers from what is now properly identified as "Sympathetic Mediated Cephalgia" a particular type of autonomic pain. With autonomic pain an abnormality in a group of nerves called a ganglion cause pain to an organ or body region. To treat sympathetic pain physicians can block a ganglion with the injection or application of medication into a specific area of the body. To therapeutically treat acute pain a physician injects or applies a local anesthetic into the affected neuronal ganglion. This type of treatment may be referred to as a nerve block.

The sphenopalatine/pterygopalatine ganglia 120 is a neuronal structure located principally in the center of the head in the pterygopalatine fossa posterior to the middle turbinate 114. The sphenopalatine/pterygopalatine ganglia 120 comprises the largest cluster of sympathetic neurons in the head outside of the brain. The sphenopalatine/pterygopalatine ganglia 120 interfaces and directs nerve impulses to the majority of the head's autonomic or parasympathetic pathways. Therefore, any abnormality or injury to this structure may cause severe pain. A nerve block of the sphenopalatine/pterygopalatine ganglia 120 may be effective in relieving a variety of pain conditions ranging from headache to lower back pain. Additionally, other disease processes such as headache disorders and other neurological conditions can be arrested, or improved by local anesthetic blockade, and/or other pharmacological augmentation or mechanical alteration of the sphenopalatine/pterygopalatine ganglia 120 and surrounding structures.

Unfortunately, because of the anatomical position of the sphenopalatine/pterygopalatine ganglia 120, the structure may be very difficult to block with a local anesthetic solution using some commonly practiced techniques. The anatomical location of the sphenopalatine/pterygopalatine ganglia 120 is dangerously close to many vital and delicate mid-brain structures. Although direct needle placement can be employed under fluoroscopic guidance to administer anesthetic to the sphenopalatine/pterygopalatine ganglia 120, most practitioners will not attempt the procedure due to the technical difficulty and extreme dangers of an aberrant needle placement.

Figure 2:
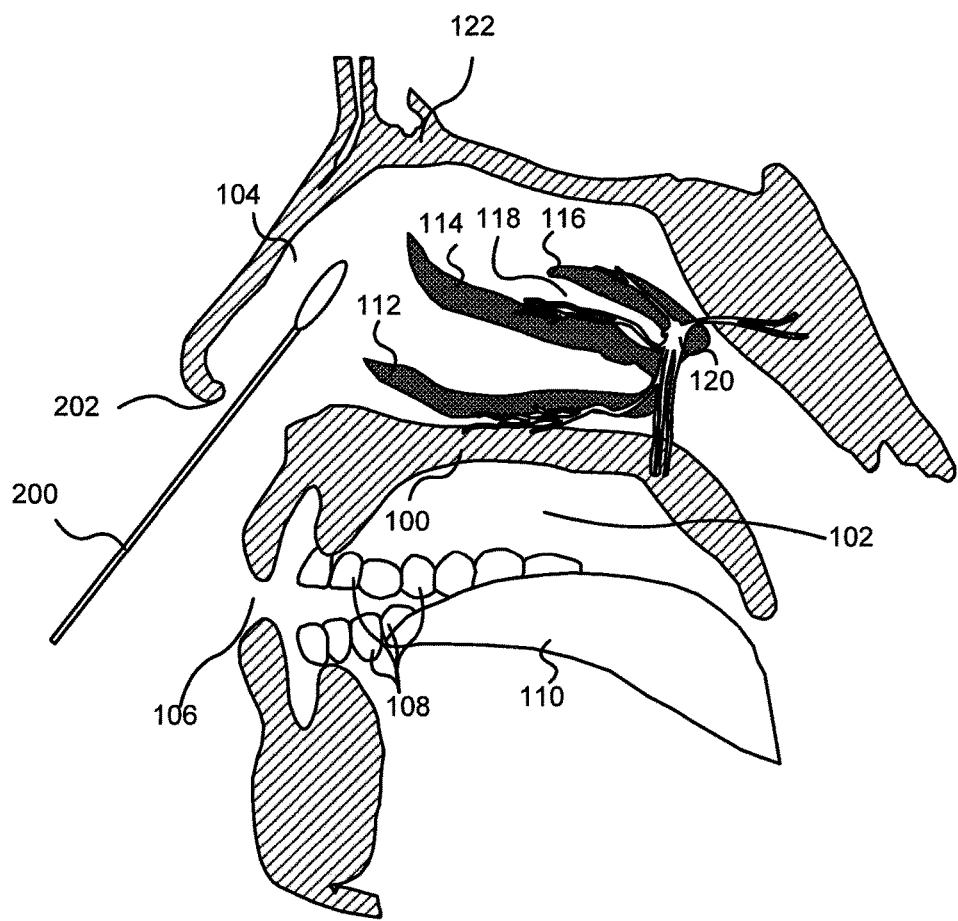
FIG. 2 is a cutaway view illustrating a prior art method of treating headaches.

As shown in the prior art illustration depicted in FIG. 2, the sphenopalatine/pterygopalatine ganglia 120 lies deep within the sphenopalatine/pterygopalatine recess 118. Conventional methods undertaken by pain specialists, neurologists, and neurosurgeons, include the use of an eight inch cotton-tipped applicator 200 saturated with a local anesthetic. Because a cotton-tipped applicator 200 is used, the procedure is referred to as the "Q-tip" procedure. The cotton-tipped applicator 200 is soaked in a vial of concentrated local anesthetic solution. In certain embodiments the anesthetic solution is lidocaine, cocaine, etidocaine or prilocaine, or other non-specified local anesthetic agents. The cotton-tipped applicator 200 is then advanced into the nostril 202 and through the nasal cavity 104. To reach the sphenopalatine/pterygopalatine ganglia 120 in the sphenopalatine/pterygopalatine recess 118, the cotton-tipped applicator 200 must be advanced into the nasal cavity 104 past the middle sinus turbinate 114 and into the sphenopalatine/pterygopalatine recess 118.

Figure 3:
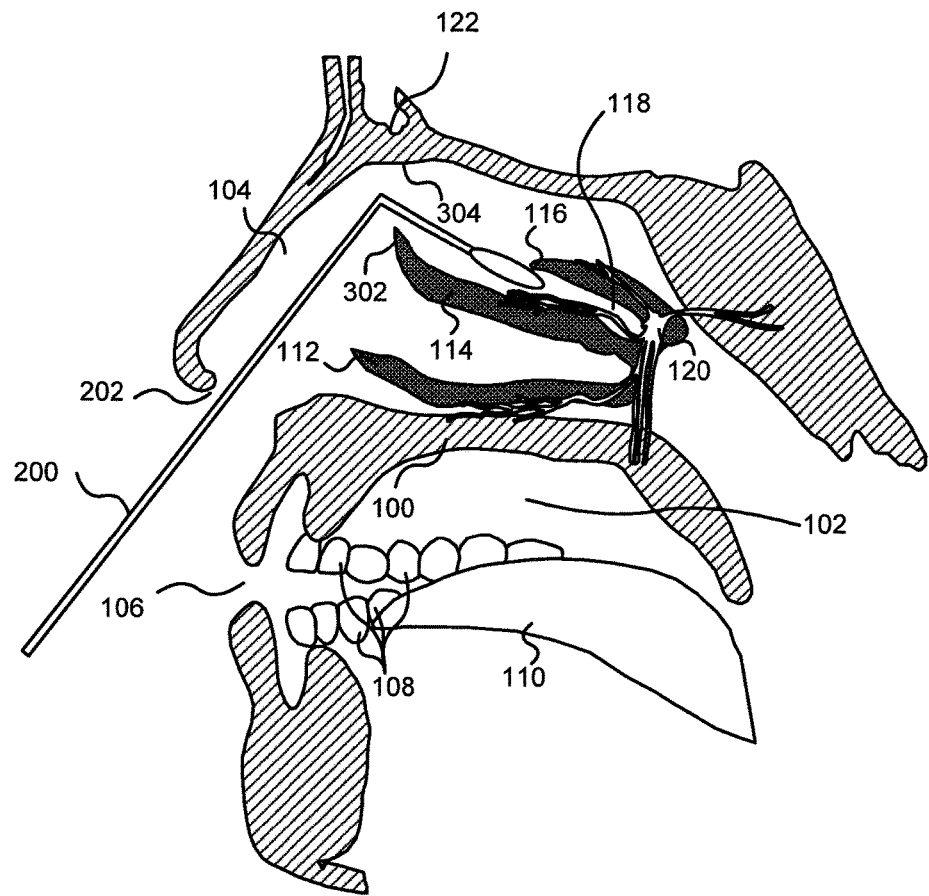
FIG. 3 is a cutaway view illustrating a prior art method of treating headaches.

FIG. 3 illustrates the tortuous path the cotton-tipped applicator 200 of the prior art must traverse to reach the sphenopalatine/pterygopalatine recess 118. To perform the procedure the patient is placed in a supine position. The cotton-tipped applicator 200 is soaked in a vial of concentrated local anesthetic solution or other pharmacologic agent. The physician then inserts the cotton-tipped applicator 200 into the patient's nostril 202 and through the nasal cavity 104. Advancing the straight, rigid cotton-tipped applicator 200 into the sphenopalatine/pterygopalatine recess 118 can be difficult and painful for the patient as the cotton-tipped applicator 200 must be inserted almost parallel to the patient's face to clear the anterior ridge 302 of the middle sinus turbinate 114. The cotton-tipped applicator 200 must then make an almost 90° bend to avoid the inferior surface 304 of the nasal bone 122 and access the sphenopalatine/pterygopalatine recess 118. The cotton-tipped applicator 200 is left in the patient's sphenopalatine/pterygopalatine recess 118 for approximately 20 minutes to allow diffusion of the local anesthetic or other pharmacologic agent through the sinus mucosa to modulate the sphenopalatine/pterygopalatine ganglia 120 to temporarily block or permanently ablate nerve transmission.

The use of a straight and rigid cotton-tipped applicator 200 that must make some fairly tortuous directional changes around some very sensitive, richly vascular, friable, highly innervated structures complicates the procedure to the point that many practitioners will not attempt it. Known complications include extreme patient discomfort, nosebleeds and the complications associated with nosebleeds including venous-irritating nuisances, arterial hemorrhaging, aspiration, hematochezia or even death. Other complications include local anesthetic toxicity, seizure, iatrogenic foreign bodies such as a broken cotton-tipped applicator 200, sinus mucosal tears and infection.

Anesthetic blockade of any neuronal structure requires direct physical interaction between the anesthetic solution and the targeted tissue. Therefore, to work, the cotton-tipped applicator 200 must deliver the anesthetic solution directly to the sphenopalatine/pterygopalatine ganglia 120. The correct placement of the cotton-tipped applicator 200 is technically challenging and many practitioners simply miss the desired structure, the sphenopalatine/pterygopalatine ganglia 120 when attempting to perform the procedure. To help make the complicated bend required to reach the sphenopalatine/pterygopalatine recess 118 many practitioners will soak the top 2 inches of the cotton-tipped applicator 200 and manipulate the stem to render it flexible so that the patient is less agitated and bleeding risks are lessened. Even with a flexible cotton-tipped applicator 200 the procedure is difficult. Common failure placements include the inferior surface 304 of the nasal bone 122 and the anterior ridge 302 of the middle sinus turbinate 114. When the cotton-tipped applicator 200 is misplaced, a "wring-out" effect may occur wherein the anesthetic is wrung out of the cotton-tipped applicator before it is delivered to the sphenopalatine/pterygopalatine ganglia 120 resulting in an ineffective procedure. Further, as discussed above, the rich vascular and neuronal structure of the nasal cavity 104 makes any misplacement of the cotton-tipped applicator 200 both dangerous and painful.

Figure 4A:
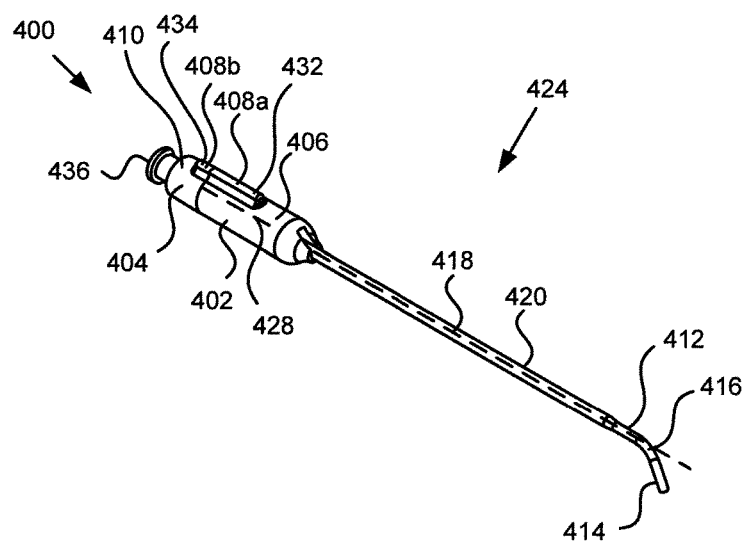
FIG. 4A is a perspective view illustrating one embodiment of an apparatus for facilitating intranasal treatment of a patient's sphenopalatine/pterygopalatine recess with a catheter hub positioned in an inserted position within a sheath hub (ready for medication delivery) in accordance with the present subject matter.
Figure 4B:
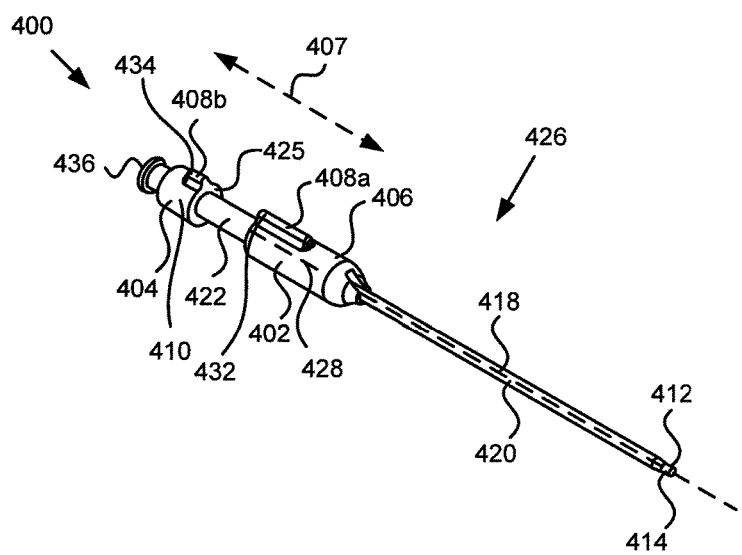
FIG. 4B is a perspective view illustrating one embodiment of an apparatus for facilitating intranasal treatment of a patient's sphenopalatine/pterygopalatine recess with a catheter hub positioned in an extended position within a sheath hub (ready for device insertion) in accordance with the present subject matter.

FIG. 4A depicts a perspective view of one embodiment of an apparatus 400 for facilitating intranasal treatment of a patient's sphenopalatine/pterygopalatine recess 118. The apparatus 400, in certain embodiments, includes the sheath hub 402, the catheter hub 404, a catheter 412, and a sheath 420. The apparatus 400 of FIG. 4A is depicted with a catheter hub 404 positioned in an inserted position 424 within a sheath hub 402. FIG. 4B depicts a perspective view of one embodiment of the apparatus 400 of FIG. 4A with the catheter hub 404 positioned in an extended position 426 within the sheath hub 402.

Figure 5A:
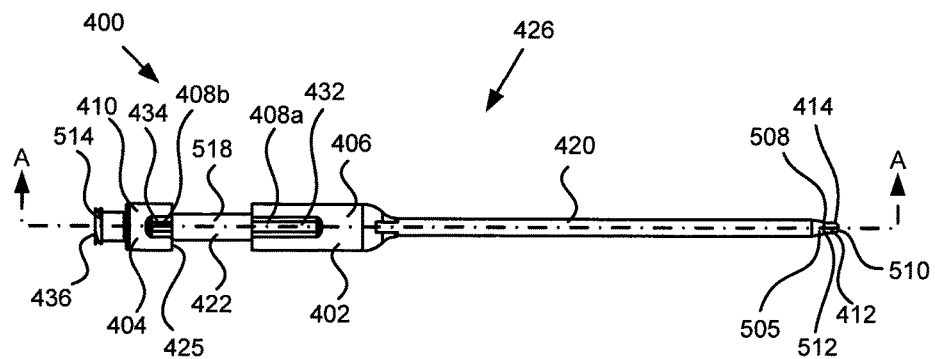
FIG. 5A is a top view illustrating one embodiment of an apparatus for facilitating intranasal treatment of a patient's sphenopalatine/pterygopalatine recess with a catheter hub positioned in an extended position within a sheath hub (ready for device insertion) in accordance with the present subject matter.
Figure 5B:
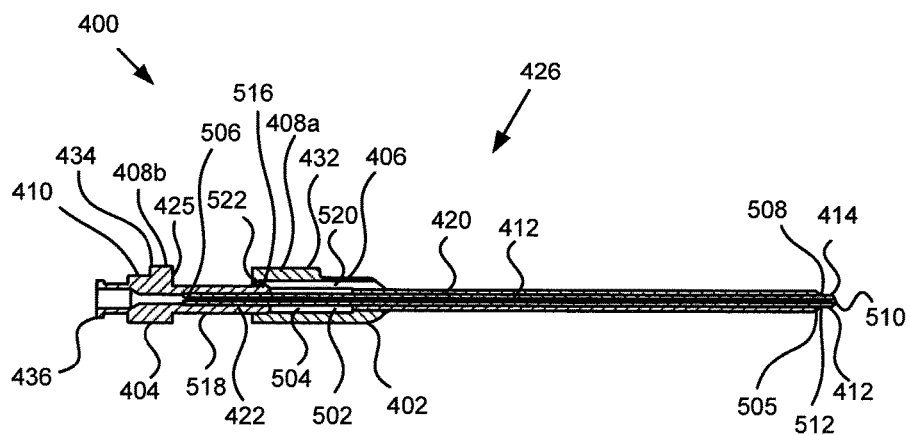
FIG. 5B is a side cutaway view illustrating one embodiment of an apparatus for facilitating intranasal treatment of a patient's sphenopalatine/pterygopalatine recess with a catheter hub positioned in an extended position within a sheath hub (ready for device insertion) in accordance with the present subject matter.

The sheath hub 402 includes an exterior surface 406 that opposes an interior surface 502 (FIG. 5B). The interior surface 502 of the catheter hub 404 defines a catheter hub receiving space 504 (FIG. 5B). At least a portion 422 of the catheter hub 404 is received within the catheter hub receiving space 504 and the catheter hub 404 is repositionable along a longitudinal axis 428 of the sheath hub 402. In certain embodiments, the catheter hub 404 is repositionable between an inserted position 424 as illustrated in FIG. 4A and an extended position 426 as illustrated in FIG. 4B.

In one embodiment, the catheter hub 404 includes a stopping surface 425. When the catheter hub 404 is fully inserted into the catheter hub receiving space 504, the stopping surface 425 of the catheter hub 404 contacts the sheath hub 402 to arrest further insertion of the catheter hub 404 within the catheter hub receiving space 504. With the catheter hub 404 fully positioned within the catheter hub receiving space 504 to the point where the stopping surface 425 contacts the sheath hub 402, the catheter hub 404 may be considered to be positioned in the fully inserted position 424 with the internal catheter being fully extended beyond the distal tip of the sheath. As the catheter hub 404 is withdrawn from within the catheter hub receiving space 504 in the direction indicated by arrows 407, the catheter hub 404 may be considered to be positioned in a fully extended position 426.

In the depicted embodiments, the profile of the sheath hub 402 and the profile of the catheter hub 404 are substantially circular. In other embodiments, the sheath hub 402 and the catheter hub 406 may have a triangular profile, a square profile, a rectangular profile, an octagonal profile, an oblong profile, or a profile having any other geometric shape.

A catheter 412 is coupled to the catheter hub 404 at a coupling end 506 (see FIG. 5B) of the catheter 412. An insertion end (distal tip) 414 of the catheter 412 includes an intrinsic curvature 416 with respect to a longitudinal axis 418 of the catheter 412. The insertion end 414 of the catheter 412 is disposed opposite the coupling end 506 of the catheter 412. The intrinsic curvature 416 of the insertion end 414 of the catheter 412 causes the insertion end 414 of the catheter 412 to bend when advanced beyond the distal tip of the sheath 420. When the apparatus 400 is inserted into the patient's nasal cavity 104 the intrinsic curvature 416 of the insertion end 414 is retracted into the sheath 420 until the physician or other medical professional advances the catheter beyond the distal tip of the sheath 420 into the space directly above the patient's sphenopalatine/pterygopalatine recess 118 without contacting the delicate surrounding structures of the patient's nasal cavity 104.

When the catheter 412 is first inserted into the patient's nasal cavity 104, the catheter 412 must travel in a relatively straight path past the anterior ridge 302 of the middle sinus turbinate 114 to access the patient's sphenopalatine/pterygopalatine recess 118. Therefore, upon insertion into the patient's nasal cavity, the catheter 412 should be relatively straight. In order to straighten the intrinsic curvature 416 of the insertion end 414 of the catheter 412, the catheter 412 is received within a sheath 420 which has a sufficient structural rigidity to straighten the intrinsic curvature 416 of the insertion end 414 of the catheter 412. The sheath 420 is coupled to the sheath hub 402 and the catheter 412 is retracted within the sheath 420.

Because the catheter 412 is coupled to the catheter hub 404 and the sheath 420 is coupled to the sheath hub 402, when the catheter hub 404 is positioned in the extended position 426 the catheter 412 is withdrawn into the sheath 420 as illustrated in FIG. 4B. With the catheter 412 withdrawn into the sheath 420, the structural rigidity of the sheath 420 straightens the intrinsic curvature 416 of the insertion end 414 of the catheter 412 allowing the physician or other medical professional to manipulate the insertion end 414 of the catheter 412 past the anterior ridge 302 of the middle sinus turbinate 114.

Once the insertion end 414 of the catheter 412 has passed the anterior ridge 302 of the middle sinus turbinate 114, the physician or other medical professional can advance the catheter hub 404 to the inserted position 424. With the catheter hub 404 repositioned in the inserted position 424 the intrinsic curvature 416 of the insertion end 414 of the catheter 412 is not positioned within the sheath 420 and is therefore not straightened by the sheath 420. The intrinsic curvature 416 of the insertion end 414 of the catheter 412 causes the insertion end 414 of the catheter 412 to bend. The bend in the catheter 412 allows the physician or other medical professional to direct the insertion end 414 of the catheter 412 into the patient's sphenopalatine/pterygopalatine recess 118 where the physician or other medical professional can deliver treatment to the patient's sphenopalatine/pterygopalatine ganglia 120.

While the present discussion is directed to access of the sphenopalatine/pterygopalatine recess 118 to treat the sphenopalatine/pterygopalatine ganglia 120, one of skill in the art will recognize that in other embodiments, the apparatus 400 may be used to access other areas of a patient. For example, the apparatus 400 may be used by a physician or other medical professional to position the insertion end 414 of the catheter 412 in any area on the patient that is not linear disposed with reference to the entry point. Examples of such areas may include a patient's aural cavity, veins, arteries, etc.

In certain embodiments, the treatment delivered may be a dispensing of a nerve blockage to the sphenopalatine/pterygopalatine ganglia 120 through the catheter 412. In other embodiments, the catheter 412 may include an electrode configured to deliver an electrical stimulation to the sphenopalatine/pterygopalatine ganglia 120. One of skill in the art will recognize other medical treatments may be delivered to the sphenopalatine/pterygopalatine ganglia 120.

When the physician or other medical professional inserts the insertion end of the catheter 412 into the patient's nasal cavity, the physician's or other medical professional's view of the insertion end 414 of the catheter 412 may be obstructed by the surrounding structure of the patient's nose. Accordingly, the physician or other medical professional cannot see the orientation of the intrinsic curvature 416 or insertion end 414 of the catheter 412 to determine whether or not the intrinsic curvature 416 is oriented in a position to advance the insertion end 414 of the catheter 412 into the patient's sphenopalatine/pterygopalatine recess 118. To aid the physician or other medical professional in advancing the insertion end 414 of the catheter 412 into the patient's sphenopalatine/pterygopalatine recess 118, in certain embodiments, the apparatus 400 includes a rotational orientation indicator 408. In one embodiment, the rotational orientation indicator 408 identifies a rotational orientation of the intrinsic curvature 416 of the catheter 412 to aid the physician or other medical professional in determining the orientation of the insertion end 414 of the catheter. In certain embodiments, the rotational orientation indicator 408 may be a visual indicator such as a line, a dot, or other indication, positioned on an exterior surface 406 of the sheath hub 402, an exterior surface 410 of the catheter hub 404, or both.

In the embodiment illustrated in FIGS. 4A and 4B, the rotational orientation indicator 408 includes a first rotational orientation indicator 408a positioned on an exterior surface 406 of the sheath hub 402 and a second rotational orientation indicator 408b positioned on an external surface 410 of the catheter hub 404. In other embodiments, only one of the sheath hub 402 or the catheter hub 404 includes a rotational orientation indicator 408.

In one embodiment, the rotational orientation indicator 408a on the sheath hub 402 is a raised ridge 432 that extends longitudinally along at least a portion of the sheath hub 402. The raised ridge 432 extends substantially perpendicularly from the exterior surface 406 of the sheath hub 402 to provide a physician or other medical professional tactile feedback as to the orientation of the intrinsic curvature 416 of the catheter 412. Thus, when the physician or other medical professional advances the insertion end 414 of the catheter 412 into a patient's nasal cavity 104, the physician or other medical professional can focus their visual attention on other factors that may affect the procedure such as the depth of the catheter 412 within the patient's nasal cavity 104.

In certain embodiments, the rotational orientation indicator 408b on the catheter hub 404 may also be a raised ridge 434. In such an embodiment, the raised ridge 434 extends longitudinally along at least a portion of the catheter hub 404. The raised ridge 432 extends substantially perpendicularly from the exterior surface 410 of the catheter hub 404 to provide a physician or other medical professional tactile feedback as to the orientation of the intrinsic curvature 416 of the catheter 412. In embodiments where both the sheath hub 402 and the catheter hub 404 include raised ridges 432 and 434 that act as rotational orientation indicators 408, the physician or other medical professional can determine the orientation of the intrinsic curvature 416 of the catheter 412 regardless of which component (the catheter hub 404 or the sheath hub 402) the physician or other medical professional is manipulating.

In certain embodiments, the raised ridges 432 and 434 on the sheath hub 402 and the catheter hub 404 are aligned along the same axis. In other embodiments, the raised ridge 432 on the sheath hub 402 may be offset from the raised ridge 434 on the catheter hub 404. In yet another embodiment, as discussed above, only one of the sheath hub 402 or the catheter hub 404 includes a rotational orientation indicator 408. In such an embodiment, the apparatus 400 may include either raised ridge 432 on the exterior surface 406 of the sheath hub 402 or raised ridge 434 on the exterior surface 410 of the catheter hub 404.

In one embodiment, the apparatus 400 includes a treatment receiving port 436 that receives a medicinal treatment. For example, in certain embodiments, the treatment receiving port 436 is coupleable to a syringe or other medication delivery device. The treatment receiving port 436 is communicable in fluid communication with the catheter 412 such that medication can be delivered through the catheter 412 to the sphenopalatine/pterygopalatine ganglia 120.

In other embodiments, other treatment delivery devices may be coupled to the treatment receiving port 436. For example, in one embodiment, the treatment delivery device may include an electrical stimulation device configured to transmit an electrical current to the apparatus 400. In such an embodiment, the catheter 412 may include an electrical conduit that conducts a flow of electricity from the treatment receiving port 436 to the insertion end 414 of the catheter 412. An electrode positioned on the insertion end 414 of the catheter 412 delivers the electrical current to the patient.

FIG. 5A depicts a top view of one embodiment of an apparatus 400 for facilitating intranasal treatment of a patient's sphenopalatine/pterygopalatine recess 118. In the embodiment depicted FIG. 5A, the catheter hub 404 is positioned in the extended position 426. In certain embodiments, the sheath 420 includes an introduction end 505 that is sloped to a vertex 508 such that the entire introduction end 505 of the sheath 420 forms a smooth slope without any edges to catch on the tissue of the patient's nasal cavity 104.

In one embodiment, the insertion end 414 of the catheter 412 is curved such that a tip 510 of the insertion end 414 of the catheter 412 is rounded. By including a rounded tip 510 on the insertion end 414 of the catheter 412, the physician or other medical professional is less likely to catch or snag the delicate tissue of the patient's nasal cavity 104 with the insertion end 414 of the catheter 412. As further described below, in certain embodiments, when the catheter hub 404 is positioned in the extended position 426, the vertex 508 at the introduction end 505 of the sheath 420 aligns with a beginning of the curve of the rounded tip 510 of the catheter 412 such that a transition 512 between the catheter 412 and the sheath 420 is continuous, smooth and substantially edge free. A smooth transition 512 between the catheter 412 and the sheath 420 helps to avoid catching tissue within the patient's nasal cavity 104.

In certain embodiments, the treatment receiving port 436 includes a coupling member 514 for coupling the apparatus 400 to the treatment delivery device. For example, in one embodiment, the coupling member 514 may be a plurality of threads disposed around the circumference of the treatment receiving port 436. The threads of the coupling member 514 engage threads on a syringe or other treatment delivery device to couple the treatment delivery device to the treatment receiving port 436.

FIG. 5B depicts a side cutaway view of one embodiment of an apparatus 400 for facilitating intranasal treatment of a patient's sphenopalatine/pterygopalatine recess 118. In the embodiment depicted FIG. 5B, the catheter hub 404 is positioned in the extended position 426. The embodiment depicted in FIG. 5B is taken along line A-A of FIG. 5A and more clearly illustrates one embodiment of the interior surface 502 of the sheath hub 402 and the catheter hub receiving space 504.

In certain embodiments, the sheath hub 402 has an exterior surface 406 that opposes an interior surface 502. The interior surface 502 of the sheath hub 402 defines a catheter hub receiving space 504. A portion 422 of the catheter hub 404 has a reduced diameter and is slideably received within the catheter hub receiving space 504 such that the catheter hub 404 is repositionable in a lengthwise direction along the longitudinal axis 428 (see FIGS. 4A and 4B) of the sheath hub 402.

In certain embodiments, the apparatus 400 includes an arresting element 516 on either the catheter hub 404 or the sheath hub 402. In the embodiment illustrated in FIG. 5B, the arresting element 516 is a flange that is coupled to and extends perpendicularly from an outer surface 518 of the reduced diameter portion 422 of the catheter hub 404.

In one embodiment, the apparatus 400 also includes an engagement element 520 on either the catheter hub 404 or the sheath hub 402. In the embodiment illustrated in FIG. 5B, the engagement element 520 is a recess extending longitudinally along the interior surface 502 of the sheath hub 402. The flange of the arresting element 516 is positioned within and travels along the recess of the engagement element 520 when the catheter hub 404 is repositioned along the longitudinal axis 428 of the sheath hub 402. Cooperation between the arresting element 516 and the engagement element 520 allows the catheter hub 404 to be slideably received within the catheter hub receiving space 504 while limiting rotation of the catheter hub 404 with respect to the sheath hub 402. Accordingly, in certain embodiments, the flange of the arresting element 516 is continuously engaged within the recess of the engagement element 520 when the catheter hub 404 is repositioned within along the longitudinal axis 428 of the sheath hub 402. Engagement between the arresting element 516 and the engagement element 520 prevents rotation of the sheath hub 402 with respect to the catheter hub 404.

By limiting rotation of the catheter hub 404 with respect to the sheath hub 402, the physician or other medical professional can determine the orientation of intrinsic curvature 414 of the catheter 412 by the position of the rotational orientation indicator 408a on the catheter hub 404 and the rotational orientation indicator 408b on the sheath hub 402 may be unnecessary.

In certain embodiments, the apparatus 400 also includes a stopping element 522 coupled to either the catheter hub 404 or the sheath hub 402. The stopping element 522 is configured to engage the arresting element 516 to stop the catheter hub 404 from being removed from the catheter hub receiving space 504. In the embodiment illustrated in FIG. 5B, the stopping element 522 is a substantially rigid wall that engages the arresting element 516 to stop the catheter hub 404 from being removed from the catheter hub receiving space 504. In certain embodiments, the stopping element 522 also facilitates alignment of the vertex 508 at the introduction end 505 of the sheath 420 with the beginning of the curve of the rounded tip 510 of the catheter 412 such that the transition 512 between the catheter 412 and the sheath 420 is continuous, smooth and substantially edge free when the catheter hub 404 is positioned in the extended position 426.

Of course, one of skill in the art will recognize that in certain embodiments, the position of the arresting element 516, the engagement element 520, and the stopping element 522 may be reversed. For example, in one embodiment, the arresting element 516 may be coupled to the interior surface 502 of the sheath hub 402 and the recess of the engagement element 520 may be positioned in the outer surface 518 of the reduced diameter portion 506 of the catheter hub 404. Similarly, in one embodiment, the stopping element 522 may be coupled to the reduced diameter portion 506 of the catheter hub 404 to restrict the catheter hub 404 from being removed from within the catheter hub receiving space 504 in the sheath hub 402.

Figure 6A:
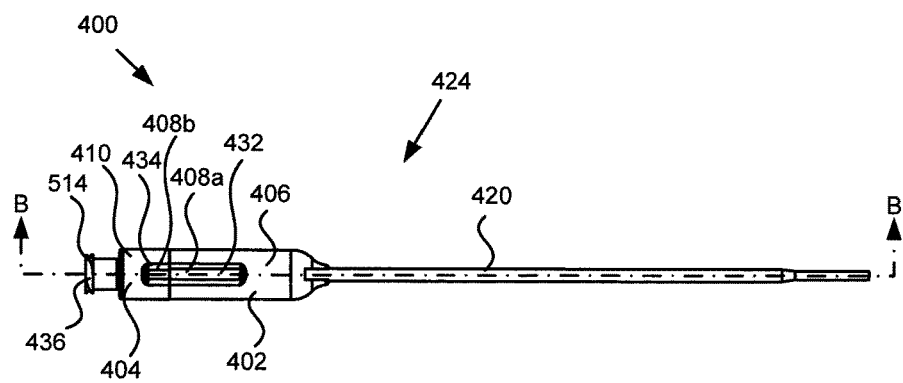
FIG. 6A is a top view illustrating one embodiment of an apparatus for facilitating intranasal treatment of a patient's sphenopalatine/pterygopalatine recess with a catheter hub positioned in an inserted position within a sheath hub (ready for medication delivery) in accordance with the present subject matter.

FIG. 6A depicts a top view of one embodiment of an apparatus 400 for facilitating intranasal treatment of a patient's sphenopalatine/pterygopalatine recess 118. In the embodiment illustrated in FIG. 6A, the catheter hub 404 is positioned in the inserted position 424.

Figure 6B:
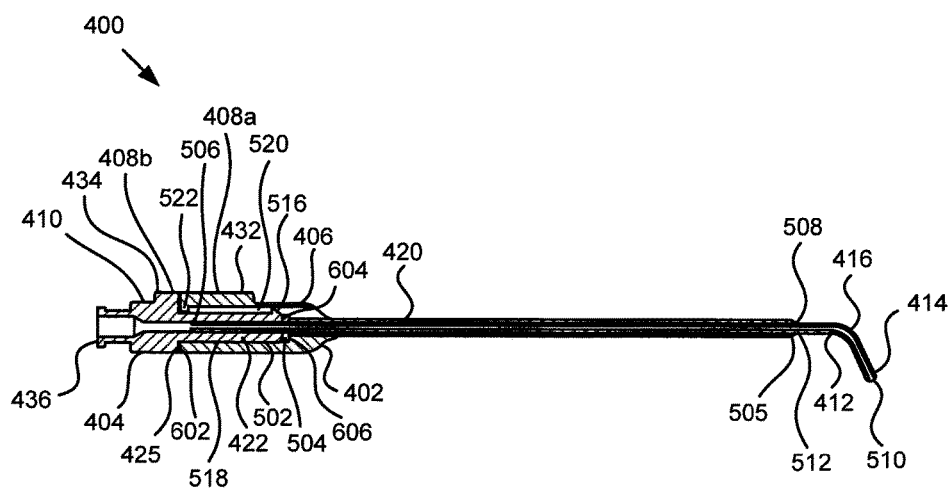
FIG. 6B is a side cutaway view illustrating one embodiment of an apparatus for facilitating intranasal treatment of a patient's sphenopalatine/pterygopalatine recess with a catheter hub positioned in an inserted position within a sheath hub (ready for medication delivery) in accordance with the present subject matter.

FIG. 6B is a side cutaway view of one embodiment of an apparatus for facilitating intranasal treatment of a patient's sphenopalatine/pterygopalatine recess 118. In the embodiment depicted FIG. 6B, the catheter hub 404 is positioned in the inserted position 424. The embodiment depicted in FIG. 6B is taken along line B-B of FIG. 6A.

In one embodiment, when the catheter hub 404 is fully inserted into the catheter hub receiving space 504, the stopping surface 425 of the catheter hub 404 contacts an end 602 of the sheath hub 402 to arrest further insertion of the catheter hub 404 within the catheter hub receiving space 504. In other embodiments, an end 604 of the reduced diameter portion 422 of the catheter hub 404 contacts an interior wall 606 within the catheter hub receiving space 504 to arrest further insertion of the catheter hub 404 within the catheter hub receiving space 504. With the catheter hub 404 fully positioned within the catheter hub receiving space 504 to the point where the stopping surface 425 contacts the sheath hub 402, the catheter hub 404 may be considered to be positioned in the fully inserted position 424.

Figure 7:
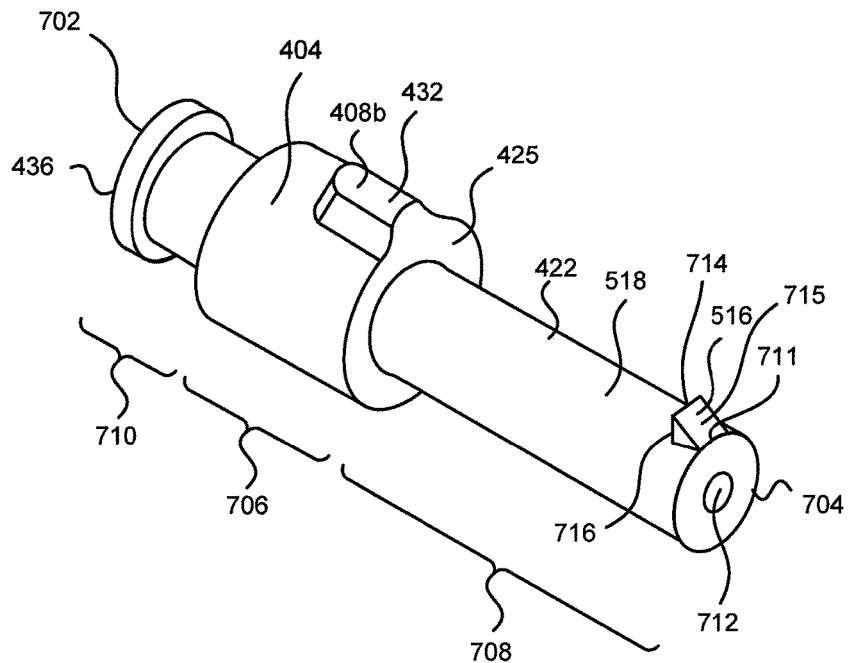
FIG. 7 is a perspective view illustrating one embodiment of a catheter hub in accordance with the present subject matter.

FIG. 7A depicts a perspective view of one embodiment of a catheter hub 404 according to the present disclosure. In the embodiment illustrated in FIG. 7A, the sheath hub 402 and the catheter 412 have been omitted to better illustrate the catheter hub 404.

In certain embodiments, the catheter hub 404 includes a treatment receiving end 702 disposed opposite a treatment delivery end 704. In one embodiment, the catheter hub 404 includes a manipulation portion 706, an insertion portion 708, and a coupling portion 710. In the depicted embodiment, the manipulation portion 706, the insertion portion 708, and the coupling portion 710 are substantially cylindrical. In other embodiments, the manipulation portion 706, the insertion portion 708, and/or the coupling portion 710 may have triangular profiles, square profiles, rectangular profiles, octagonal profiles, oblong profile, or a profile having any other geometric shape.

In one embodiment, the insertion portion 708 of the catheter hub 404 includes the reduced diameter portion 422 of the catheter hub 404. The insertion portion 708, in certain embodiments, begins at the stopping surface 425 of the catheter hub 404 and extends to the treatment delivery end 704 of the catheter hub 404.

The coupling portion 710 of the catheter hub 404 is positioned opposite the insertion portion 708 and includes the treatment receiving port 436. Anesthetics, medications, an electrical current, or any other treatment is received at the treatment receiving port 436 and delivered to the treatment delivery end 704 through a lumen 712 disposed through the catheter hub 404 from the treatment receiving end 702 to the treatment delivery end 704. When a catheter 412 is positioned in the lumen 712, the catheter receives the treatment and delivers it to a desired area such as the patient's sphenopalatine/pterygopalatine recess 118.

The manipulation portion 706 of the catheter hub 404, in certain embodiments, has an increased diameter with respect to the insertion portion 708 and is positioned between the coupling portion 710 and the insertion portion 708. The increased diameter of the manipulation portion 706 of the catheter hub 404 facilitates manipulation of the catheter hub 404 by the physician or other medical professional.

The arresting element 516 is coupled to and extends substantially perpendicularly from the outer surface 518 of the insertion portion 708 of the catheter hub 404. The arresting element 516, in one embodiment, includes a sloped surface 715. For example, in one embodiment an end 711 of the arresting element 516 adjacent the treatment delivery end 704 of the catheter hub 404 extends from the outer surface 518 of the insertion portion 708 of the catheter hub 404 a distance that is substantially less than an end 714 of the arresting element 516 closer to the treatment receiving end 702 of the catheter hub 404. The sloped surface 715 of the arresting element 516 allows the flange of the arresting element 516 to be inserted past the stopping element 522 and into the recess of the engagement element 520. A rear surface 716 of the arresting element 516 extends substantially perpendicularly from the outer surface 518 of the reduced diameter portion 422 of the catheter hub 404. When the catheter hub 404 is withdrawn from within the catheter hub receiving space 504, the rear surface 716 of the arresting element 516 engages the stopping element 522 to stop the catheter hub 404 from being removed from within the catheter hub receiving space 504. In certain embodiments, the interaction between the rear surface of the arresting element 516 and the stopping element 522 positions the catheter 412 within the sheath 420 such that the vertex 508 at the introduction end 505 of the sheath 420 aligns with a beginning of the curve of the rounded tip 510 of the catheter 412. In this position the transition 512 between the catheter 412 and the sheath 420 is continuous, smooth and substantially edge free.

Figure 8A:
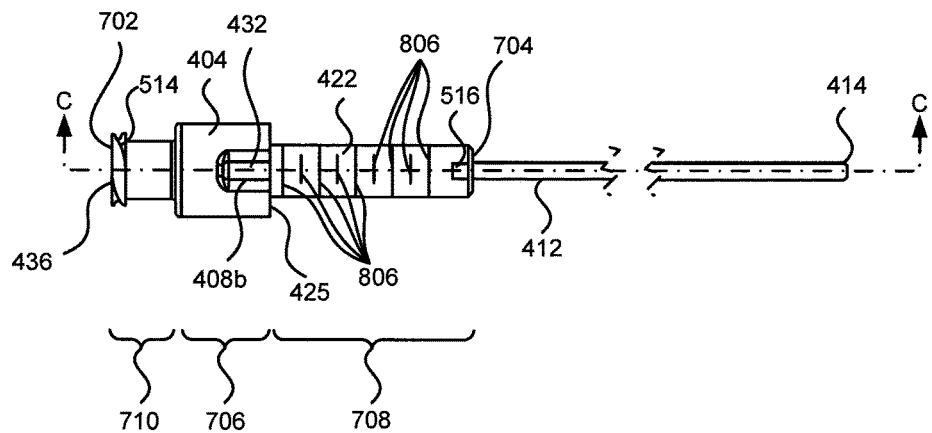
FIG. 8A is a top view illustrating one embodiment of a catheter hub and a catheter in accordance with the present subject matter.

FIG. 8A depicts a side view of one embodiment of a catheter hub 404 and a catheter 412 according to the present disclosure. In the embodiment illustrated in FIG. 8A, the threads of the coupling member 514 are more clearly illustrated. In other embodiments, the coupling member 514 may be a snap fit attachment, a rim for chemically adhering a treatment delivery device, or any other means for attaching or affixing the treatment delivery device to the catheter hub 404.

In certain embodiments, the catheter hub 404 includes a plurality of depth indicators 806 disposed along the insertion portion 708 of the catheter hub 404 at regular intervals. In the embodiment illustrated in FIG. 8A, the depth indicators 806 are lines positioned around the circumference of the insertion portion 708 of the catheter hub 404. In other embodiments, the depth indicators 806 may include other shapes, such as dots, squares, circles, triangles, or any other visual indicator. In one embodiment, the depth indicators 806 may also include a numerical indication of a depth of the catheter hub 404 within the catheter hub receiving space 504.

In performing an initial nerve block, with the catheter hub 404 positioned in the extended position 426, the physician or other medical professional advances the sheath 420 and the catheter 412 into the patient's nasal cavity 104. Once the insertion end 414 of the catheter has passed the anterior ridge 302 of the middle sinus turbinate 114, the physician or other medical professional advances the catheter hub 404 deeper within the catheter hub receiving space 504 causing the insertion end 414 of the catheter 412 to advance past the introduction end 505 of the sheath 420. Once the insertion end 414 of the catheter 412 is advanced to a position where the sheath 420 no longer contains the intrinsic curvature 416 of the catheter 412, the catheter 412 bends. Because the physician or other medical professional knows the direction in which the catheter 412 is bent by the orientation of the rotational orientation indicator 408, the physician or other medical professional can direct the insertion end 414 of the catheter 412 into the sphenopalatine/pterygopalatine recess 118 to deliver a nerve block or other treatment to the sphenopalatine/pterygopalatine ganglia 120.

As will be evident to one of skill in the art, the anatomy of a patient's nasal cavity 104 varies from individual to individual. Accordingly, certain patient's will have a deeper sphenopalatine/pterygopalatine recess 118 than others. The depth indicators 806 on the insertion portion 708 of the catheter hub 404 allow a physician or other medical professional to determine a depth of the insertion end 414 of the catheter 412 when the insertion end 414 of the catheter 412 is positioned within the patient's sphenopalatine/pterygopalatine recess 118. In one embodiment, during an initial treatment of a particular patient's sphenopalatine/pterygopalatine ganglia 120 the physician or other medical professional may record a depth of the patient's sphenopalatine/pterygopalatine recess 118. In subsequent treatments of the patient's sphenopalatine/pterygopalatine ganglia 120, the physician or other medical professional can use the recorded depth as a guide.

Figure 8B:
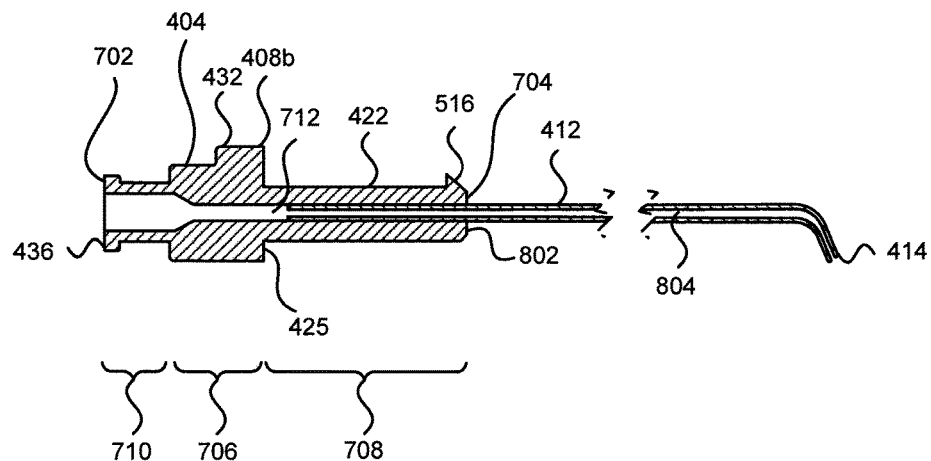
FIG. 8B is a side cutaway view illustrating one embodiment of a catheter hub and a catheter in accordance with the present subject matter.

FIG. 8B depicts a cutaway view of one embodiment of a catheter hub 404 according to the present disclosure. The embodiment depicted in FIG. 8B is taken along line C-C of FIG. 8A.

In certain embodiments, the catheter 412 is positioned within the lumen 712 in the catheter hub 404 and extends at least partially into the lumen 712. In other embodiments, the catheter 412 may be affixed to the end surface 802 at the treatment delivery end 704 of the catheter 412. In either embodiment, the catheter 412 is communicable in fluid communication with the lumen 712 to deliver medication, an anesthetic, or other chemical to the insertion end 414 of the catheter 412 where it can be dispensed to the patient.

In other embodiments, a electrical conduit, such as a wire, is positioned through the lumen 712 in the catheter 412 and through a lumen 804 in the catheter. In such an embodiment, the electrical conduit may be coupled to an electrical source to deliver an electrical current to an electrode positioned at the insertion end 414 of the catheter 412. The electrode is configured to deliver the electrical current to the patient.

Figure 9A:
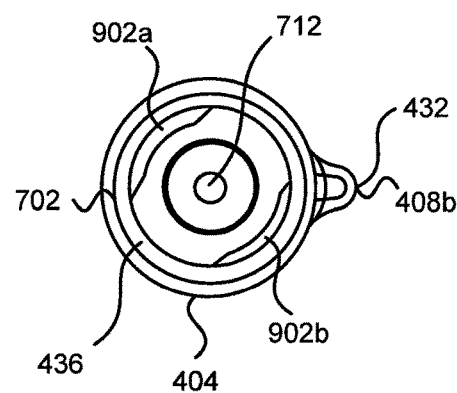
FIG. 9A is an end view depicting one embodiment of a catheter hub taken in the direction of the treatment receiving end of the catheter hub in accordance with the present subject matter.

FIG. 9A is an end view depicting one embodiment of a catheter hub 404 according to the present disclosure. The embodiment illustrated in FIG. 9A is taken in the direction of the treatment receiving end 702 of the catheter hub 404.

In certain embodiments, the catheter hub 404 includes one or more coupling flanges 902a and 902b positioned on an inner circumference 904 of the treatment receiving port 436. In such an embodiment, the coupling flanges 902 are configured to couple a syringe or other treatment delivery device to the catheter hub.

Figure 9B:
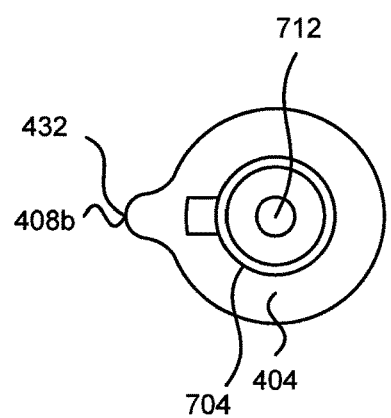
FIG. 9B is an end view depicting one embodiment of a catheter hub taken in the direction of the treatment delivery end of the catheter hub in accordance with the present subject matter.

FIG. 9B is an end view depicting one embodiment of a catheter hub 404 according to the present disclosure. The embodiment illustrated in FIG. 9A is taken in the direction of the treatment delivery end 704 of the catheter hub 404.

Figure 10A:
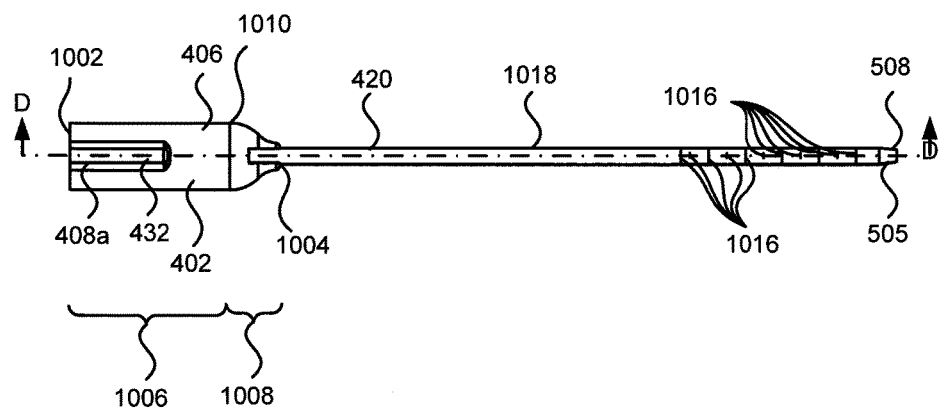
FIG. 10A is a top view illustrating one embodiment of a sheath hub and a sheath in accordance with the present subject matter.

FIG. 10A depicts a top view of one embodiment of the sheath hub 402 coupled to a sheath 420 according to the present disclosure. The sheath hub 402, in certain embodiments, includes a catheter hub receiving end 1002 and a sheath receiving end 1004. In the embodiment illustrated in FIG. 10A, the sheath 420 is coupled to the sheath receiving end 1004 of the sheath hub 402.

In certain embodiments, the sheath hub 406 includes a substantially cylindrical portion 1006 and a tapered portion 1008. Disposed within the cylindrical portion 1006 is the catheter hub receiving space 504. In certain embodiments, the catheter hub receiving space 504 is also a substantially cylindrical void in the sheath hub 406. In such embodiments, the insertion portion 708 of the catheter hub 404 is also cylindrical such that the insertion portion 708 of the catheter hub 404 may be received within the catheter hub receiving space. In other embodiments, the shape of the insertion portion 708 of the catheter hub 404 and the shape of the void of the catheter hub receiving space 504 may be any other geometric shape while the outer surface 406 of the sheath hub 402 remains cylindrical. Of course, in one embodiment, the opposite may be true. That is, in certain embodiments, the outer surface 406 of the sheath hub 402 may be a shape other than cylindrical while the shape of the insertion portion 708 of the catheter hub 404 and the shape of the void of the catheter hub receiving space 504 are cylindrical.

The tapered portion 1008 of the sheath hub 402 extends from the cylindrical portion 1006 to the sheath receiving end 1004 of the sheath hub 402. The diameter of the sheath hub 402 at the sheath receiving end 1004 is substantially smaller than the diameter of the sheath hub 402 at the interface 1010 between the cylindrical portion 1006 and the tapered portion 1008 such that the tappered portion 1008 of the sheath hub 402 is sloped towards the tappered portion 1008 of the sheath hub 402.

In certain embodiments, a the sheath 420 may include a plurality of depth indicators 1016 disposed along at least a portion of an exterior surface 1018 of the sheath 420 at regular intervals. In the embodiment illustrated in FIG. 10A, the depth indicators 1016 are lines positioned on the exterior surface 1018 of the sheath 420. In other embodiments, the depth indicators 1016 may include other shapes, such as dots, squares, circles, triangles, or any other visual indicator. In one embodiment, the depth indicators 1016 may also include a numerical indication of a depth of the sheath 420 when the sheath 420 is positioned within a patient's nasal cavity 104.

As discussed above, the anatomy of a patient's nasal cavity 104 varies from individual to individual. Accordingly, a depth of the anterior ridge 302 of the middle sinus turbinate 114 varies from patient to patient. During an initial treatment, a physician or other medical professional may use the depth indicators 1016 on the sheath 420 to record a depth of the anterior ridge 302 of the middle sinus turbinate 114 for a particular patient. In certain embodiments, the physician or other medical professional may also record a depth of the inferior surface 304 of the nasal bone 122 for the patient. For subsequent treatments, the physician or other medical professional can reference the recorded depths to avoid contacting or damaging the delicate tissues within the patient's nasal cavity 104.

In one embodiment, for the initial treatment, the physician or other medical professional may refer to a table (not shown) that lists an average depth anterior ridge 302 of the middle sinus turbinate 114 and an average depth of the inferior surface 304 of the nasal bone 122 for a patient according to certain characteristics of the patient. For example, in one embodiment, the table may list the average depth anterior ridge 302 of the middle sinus turbinate 114 and the average depth of the inferior surface 304 of the nasal bone 122 for a given age group. The table may also list an average depth of the sphenopalatine/pterygopalatine recess 118 for a given age group. In certain embodiments, the table may be further broken down into gender classifications. In another embodiment, the table may list the average depths according to measurements taken on the patient's external nasal anatomy.

Figure 10B:
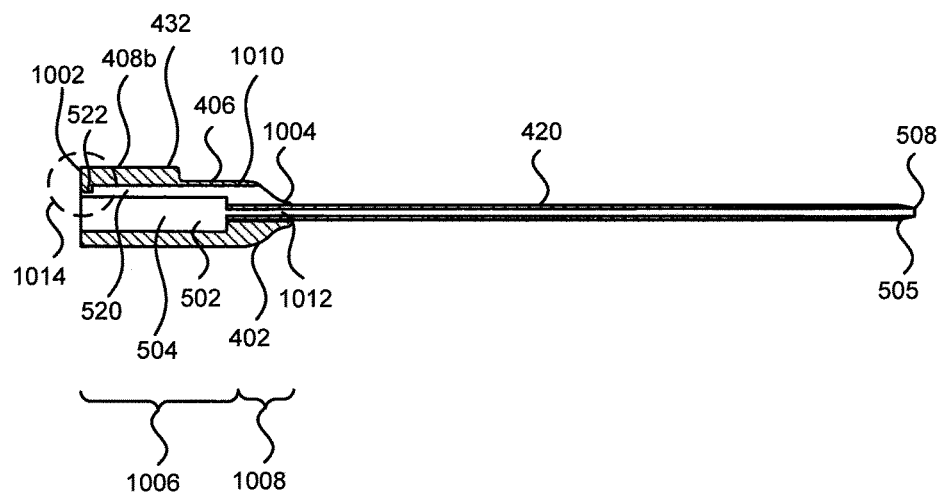
FIG. 10B is a side cutaway view illustrating one embodiment of a sheath hub and a sheath in accordance with the present subject matter.

FIG. 10B depicts a cutaway view of one embodiment of a sheath hub 402 coupled to a sheath 420 according to the present disclosure. The embodiment depicted in FIG. 10B is taken along line D-D of FIG. 10A.

In certain embodiments, the tapered portion includes a cavity 1012 that extends through the tapered portion from the catheter hub receiving space 504 in the sheath hub 402 to the sheath receiving end 1004 of the sheath hub 402. The sheath 420 is received within the cavity 1012 to couple the sheath to the sheath hub 402.

In the embodiment illustrated in FIG. 10B, the engagement element 520 is more clearly shown as a recess extending longitudinally along the interior surface 502 of the sheath hub 402. In certain embodiments, the recess of the engagement element 520 is only positioned within the cylindrical portion 1006 of the sheath hub 402. In such an embodiment, the recess of the engagement element 520 may extend from the stopping element 522 to the interface 1010 between the cylindrical portion 1006 and the tapered portion 1008. In other embodiments, such as the embodiment illustrated in FIG. 10B, the recess of the engagement element 520 may extend through the tapered portion 1008 of the sheath hub 402.

Figure 11:
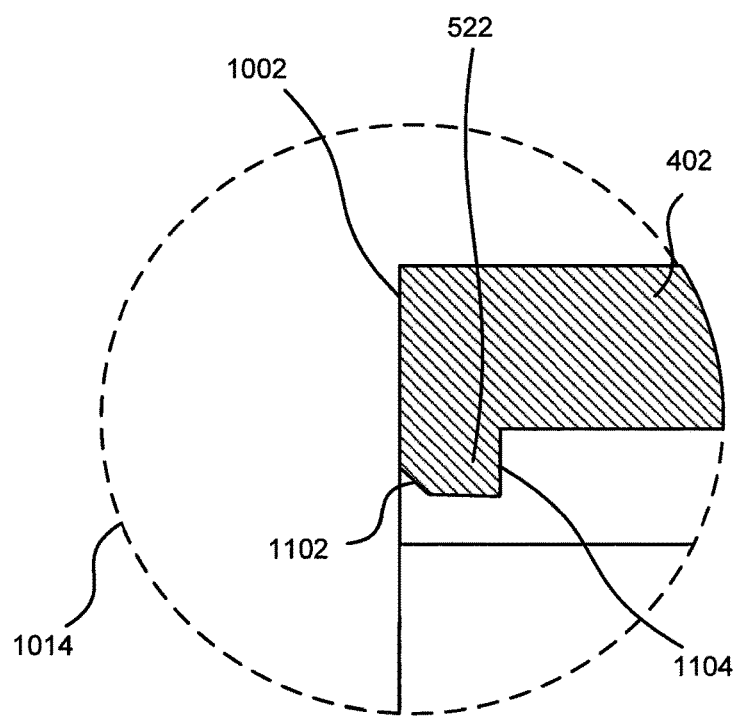
FIG. 11 is an enlarged view of an area of the sheath hub which includes the stopping element in accordance with the present subject matter.

FIG. 11 depicts an enlarged view of area 1014 of the sheath hub 402 which includes the stopping element 522 according to one embodiment of the present disclosure. In certain embodiments, the stopping element 522 includes a sloped surface 1102 disposed adjacent the catheter hub receiving end 1002 of the sheath hub 402. The sloped surface 1102 of the stopping element 522 may be engaged by the sloped surface 715 of the flange of the arresting element 516 to facilitate easy insertion of the insertion portion 708 of the catheter hub 404 into the catheter hub receiving space 504. In certain embodiments, the stopping element 522, the flange of the arresting element 516, or both may be made of a pliable or semi-pliable material to facilitate easy insertion of the insertion portion 708 of the catheter hub 404 into the catheter hub receiving space 504. In other embodiments, the entire catheter hub 402, the entire sheath hub 402, or both may be made of a pliable or semi-pliable material.

A stopping surface 1104 of the stopping element 522 extends substantially perpendicularly from the interior surface 502 of the sheath hub 402. When the catheter hub 404 is withdrawn from within the catheter hub receiving space 504 to the extended position 426, the stopping surface 1104 of the stopping element 522 engages the rear surface 716 of the arresting element 516 to stop further withdrawal of the catheter hub 404 from within the catheter hub receiving space 504.

Figure 12:
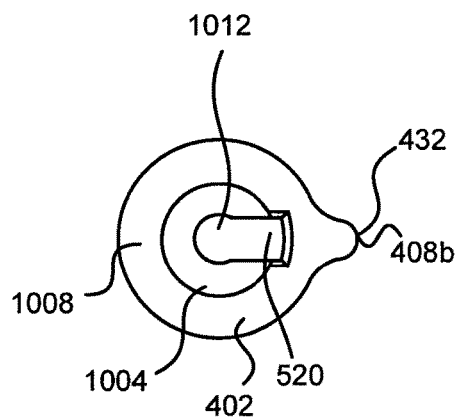
FIG. 12 is an end view depicting one embodiment of the sheath hub taken in the direction of the sheath receiving end of the sheath hub in accordance with the present subject matter.

FIG. 12 depicts an end view of one embodiment of the sheath hub 402 according to the present disclosure. The embodiment illustrated in FIG. 12 is taken in the direction of the sheath receiving end 1004 of the sheath hub 402, the sheath 420 has been removed for clarity.

In the embodiment illustrated in FIG. 12, the recess of the engagement element 520 extends through the tapered portion 1008 of the sheath hub 402 all the way to the sheath receiving end 1004. In certain embodiments, the recess of the engagement element 520 is aligned in the same rotational orientation with respect to a longitudinal axis of the sheath hub 402 as the rotational orientation indicator 408b. In other embodiments, the recess of the engagement element 520 may be offset from the rotational orientation indicator 408b.

Figure 13A:
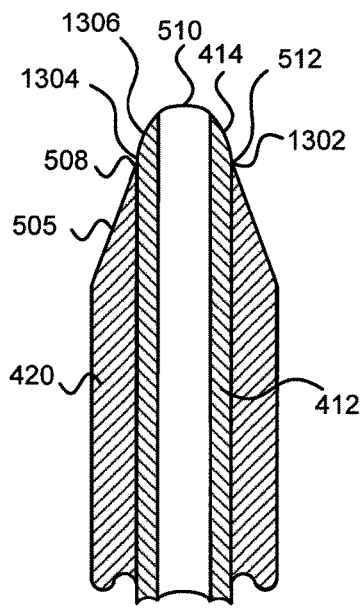
FIG. 13A is a cutaway view illustrating one embodiment of an introduction end of the sheath and an insertion end of the catheter with a vertex of the sheath aligning with a beginning of a curve of the insertion end of the catheter.

FIG. 13A illustrates a cutaway view of one embodiment of an introduction end 505 of the sheath 420 and an insertion end 414 of the catheter 412. In the embodiment illustrated in FIG. 13A, the introduction end 505 of the sheath 420 and the insertion end 414 of the catheter 412 are positioned in the position that the introduction end 505 of the sheath 420 and the insertion end 414 of the catheter 412 are placed when the catheter hub 404 (not shown) is positioned in the extended position 426.

In certain embodiments, the tip 510 of the insertion end 414 of the catheter 412 is curved 1306 such that the tip 510 is rounded. An outermost edge 1302 at the introduction end 505 of the sheath 420 is sloped to a vertex 508. In one embodiment, when the catheter hub 404 is position in the extended position 426, the vertex 508 at the introduction end 505 of the sheath 420 is aligned with a beginning 1304 of the curve 1306 of the rounded tip 510 of the catheter 412. In such an embodiment, the transition 512 between the catheter 412 and the sheath 420 is continuous, smooth and substantially edge free. In one embodiment, the fit between the catheter 412 and the sheath 420 is tight. That is, in one embodiment, there is substantially no gap between the catheter 412 and the sheath 420. In one embodiment, a lack of a gap between the catheter 412 and the sheath 420 reduces the likelihood that the vertex 508 at the introduction end 505 of the sheath 420 will snag or otherwise damage the delicate tissues within the nasal cavity 104 of the patient.

Figure 13B:
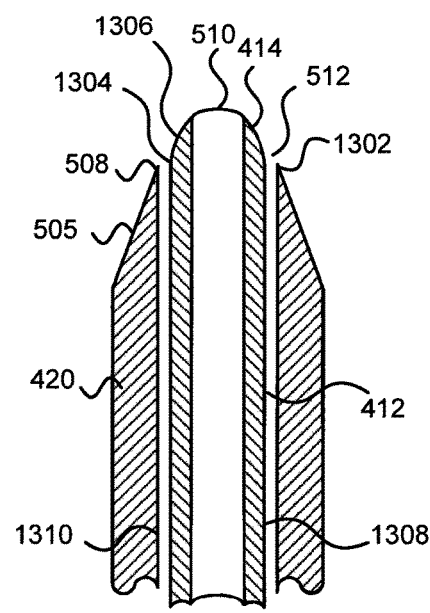
FIG. 13B is a cutaway view illustrating one embodiment of an introduction end of the sheath and an insertion end of the catheter with a vertex of the sheath out of alignment with a beginning of a curve of the insertion end of the catheter.

FIG. 13B illustrates a cutaway view of one embodiment of an introduction end 505 of the sheath 420 and an insertion end 414 of the catheter 412. In the embodiment illustrated in FIG. 13B, the outer diameter 1308 of the catheter 412 is substantially smaller than the inner diameter 1310 of the sheath 1420. In such an embodiment, the transition 512 between the catheter 412 and the sheath 420 is not smooth and the vertex 508 on the introduction end 505 of the sheath 420 may form a sharp edge that may snag or otherwise damage the delicate tissues within the nasal cavity 104 of the patient. Accordingly, in certain embodiments, the catheter 412 and the sheath 420 may be designed such that the fit between the catheter 412 and the sheath 420 is tight to avoid sharp edges.

Figure 13C:
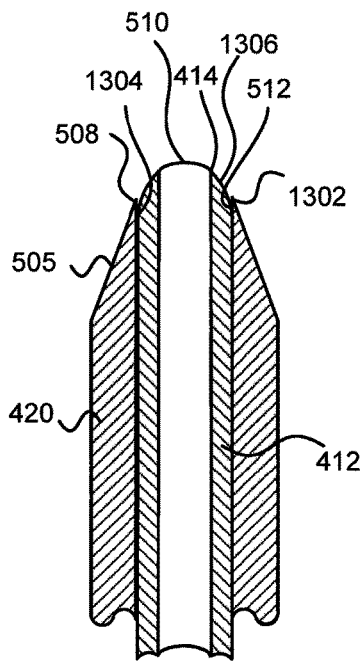
FIG. 13C is a cutaway view illustrating one embodiment of an introduction end of the sheath and an insertion end of the catheter with a vertex of the sheath out of alignment with a beginning of a curve of the insertion end of the catheter.

FIG. 13C illustrates a cutaway view of another embodiment of an introduction end 505 of the sheath 420 and an insertion end 414 of the catheter 412. In the embodiment illustrated in FIG. 13C, the catheter 412 is positioned within the sheath 420 at a position that causes the vertex 508 of the sheath 420 to extend beyond the beginning 1304 of the curve 1306 at the insertion end 414 of the catheter 412. In such an embodiment, the transition 512 between the catheter 412 and the sheath 420 is not smooth and the vertex 508 on the introduction end 505 of the sheath 420 may form a sharp edge that may snag or otherwise damage the delicate tissues within the nasal cavity 104 of the patient. Accordingly, in one embodiment, the stopping element 522 stops the withdrawal of the catheter hub 404 from within the catheter hub receiving space 504 at a position that aligns the vertex 508 on the introduction end 505 of the sheath 420 with the beginning 1304 of the curve 1306 at the insertion end 414 of the catheter 412.

Unexpectedly, advanced prototype catheters have been effectively used, with the informed consent of patients, to alleviate headache pain. Results of those procedures have been recorded and are encouraging. After 74 procedures, only four patients rated the tolerability of the procedure as either "poor" or "fair." Of the remaining patients, 24 rated tolerability as "good" and 46 rated it "excellent." This tolerability improved when patients were pretreated with intranasal anesthetic, as summarized in Table 1 below.

Of the 74 procedures recorded, no adverse events required intervention. On five occasions the nasal mucous was noted to be slightly blood-tinged, but no frank epistaxis occurred. Two procedures resulted in worsened headache, but both patients were back to their baseline headache the following day without further incident. Except for those two patients, all responded that they would have the procedure again if necessary.

On the day that SPGB was performed, 58% of patients left the office with a complete resolution of their headache, while 74% experienced significant clinical improvement as assessed by the visual analog scale (VAS). Though some patients have been lost to follow-up, significant improvement in headache severity persisted for one third of patients at one month. These results defy expected norms both in terms of clinical outcomes and predicted efficacy both of the device and the procedure. Likewise, unexpected is ostensive patient acceptance and tolerability of the procedure. Given the nature of the procedural and patient satisfaction outcomes, performance of this procedure by other than the most highly skilled, experienced and practiced surgeons, it is respectfully proposed, constitutes progress in science and the useful arts as based upon an unexpected series of results, according to the person of normal skill in the art, in this case, it is respectfully submitted, a neurologist or neurosurgeon.

TABLE 1

| Reduction in VAS | At Discharge (N = 74) |
|---|---|
| 80-100% | 43 (58%) |
| 50-79% | 12 (16%) |
| 20-49% | 3 (4%) |
| <19% | 16 (23%) |

EXAMPLES

BC sustained a head injury in a snowmobile accident nearly a decade ago and could not remember a day without a headache since. Therapy, standard medications, even narcotics failed to give him relief. Every day ended with an 9/10 headache. He experienced 100% resolution of his headache after SPGB and has remained headache free for more than a year.

AD, a highway patrolman, suffered 8/10 headaches virtually every day for years. He remained headache free for two months after SPGB. Remembering in those two months how good life could be without headaches, he tearfully requested a repeat procedure when his headaches returned. He now has a brief, painless, bi-monthly procedure and lives headache free.

Likewise, certain types of headaches are a consequence of nerve dysfunction, disrupting the dysfunctional circuits can act as a reset, allowing normal nerve function to return. For this reason, the benefit of a SPGB may last for an indefinite period of time, far beyond the effect of the local anesthetic. Accordingly, it has been learned that many patients experience an increased benefit when the procedure is repeated.

Prior teachings fail to suggest such results. For example, a randomized, double-blind, controlled trial published in the *Journal of the American Medical Association* in 1996 described rapid relief of migraine headaches in 55% of patients when they dripped topical lidocaine into the nostrils of headache sufferers. Of those who responded, 42% experienced relapse headaches, usually within the first hour. Of note, they excluded patients whose "headache had lasted more than 3 days or if the frequency of severe headaches was more than once per week."

Our patients suffered from chronic daily headaches, many with the very types of headaches excluded by this study. Because there is good scientific theory behind SPGB for several types of cephalgia, and because the potential adverse effects of the procedure are so few and so mild, we took the approach of being much more inclusive in our use of SPGB and have experienced better than expected results.

A retrospective chart review at Thomas Jefferson University in 2006 looked at a refractory chronic headache population more similar to ours, including 41 patients with transformed migraines, 12 with daily persistent headaches and 15 with "other headache diagnoses." They reported; "25.4% had complete a response, 57.1% had a partial response, 3.2% worsened, and 14.3% had no change." Their lidocaine regimen, however, was *IV lidocaine in a cardiac monitored unit over* 2-15 *days*.

It is respectfully proposed that the SphenoCath™ brand of medical device has the potential to eclipse most, if not all, published study results, simply because it more precisely and consistently delivers medication to the desired location. Direct fluoroscopy has documented the ability of the SphenoCath™ brand of medical device to deliver an infusion to the target. Furthermore, the SphenoCath™ brand of medical device extends the opportunity for SPGB from a small contingent of pain specialists, to the office practitioner, exponentially increasing patient access to the procedure.

In certain embodiments, the vertex 508 at the introduction end 505 of the sheath 420 is shielded from the delicate tissues within the nasal cavity 104 of the patient by the rounded side wall 1314 of the bulbous tip area 1310. In other embodiments, an outer diameter 1316 of the sheath 420 may be substantially smaller than an outermost diameter 1318 of the bulbous tip area 1310 such that the bulbous tip area shields the introduction end 505 of the sheath 420 from potential snags or other damage to the delicate tissues within the nasal cavity 104 of the patient. In such an embodiment, the introduction end 505 may be squared off or rounded rather than sloped as illustrated in the depicted embodiment.

The present subject matter may be embodied in other specific forms without departing from its spirit or essential characteristics. The described embodiments are to be considered in all respects only as illustrative and not restrictive. The scope of the subject matter is, therefore, indicated by the appended claims rather than by the foregoing description. All changes which come within the meaning and range of equivalency of the claims are to be embraced within their scope.

While the method and apparatus have been described in terms of what are presently considered to be the most practical, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure also includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the invention both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementations, a method or process implementations, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element, disclosed, should be understood to encompass a disclosure of the action which that physical element facilitates.

Any patents, publications, or other references, mentioned in this application, for patent, are hereby incorporated by reference. In addition, as to each term used, it should be understood that, unless its utilization in this application is inconsistent with such interpretation, common dictionary definitions should be understood, as incorporated, for each term, and all definitions, alternative terms, and synonyms such as contained in at least one of a standard technical dictionary recognized by artisans and the Random House Webster's Unabridged Dictionary, latest edition, are hereby incorporated by reference.

Finally, all references, listed in the Information Disclosure Statement or other information statement filed with the application, are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard, it should be understood that, for practical reasons, and so as to avoid adding potentially hundreds of claims, the applicant has presented claims with initial dependencies only.

Support should be understood to exist, to the degree required under new matter laws, —including but not limited to United States Patent Law 35 USC 132 or other such laws, —to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular exemplary implementations, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative exemplary implementations.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An apparatus facilitating intranasal treatment of a patient's sphenopalatine/pterygopalatine recess, the apparatus comprising:
   a sheath hub comprising a tapered distal end portion, the sheath hub having an exterior surface opposing an interior surface, wherein the exterior surface defines a diameter of the sheath hub, and wherein the interior surface defines a catheter hub receiving space;
   a catheter hub positioned longitudinally adjacent to the sheath hub and partially received within the catheter hub receiving space of the sheath hub, the catheter hub comprising a manipulation portion, an insertion portion and a coupling portion collectively forming a unitary body of the catheter hub, wherein:

(i) the manipulation portion has an increased diameter with respect to both the coupling portion and the insertion portion, the manipulation portion is located between the coupling portion and the insertion portion, the manipulation portion is located externally with respect to the sheath hub, the increased diameter of the manipulation portion is the same as the diameter of the sheath hub, and the manipulation portion defines a stopping surface of the catheter hub for contacting an adjoining end of the adjacent sheath hub to arrest further insertion of the catheter hub within the catheter hub receiving space;

(ii) the insertion portion comprises a lumen, the insertion portion extends from the stopping surface defined by the manipulation portion, and the insertion portion is slideably received within the catheter hub receiving space; and (iii) the coupling portion comprises a treatment receiving port, the treatment receiving port in fluid communication with the lumen of the insertion portion;

a sheath coupled to and extending from the tapered distal end portion of the sheath hub, and a catheter coupled to and extending from the lumen of the insertion portion of the catheter hub, wherein:

(i) an insertion end of the catheter has an intrinsic curvature specifically adapted to access the sphenopalatine/pterygopalatine recess between the patient's middle sinus turbinate and superior sinus turbinate for delivering a medication at a posterior of the sphenopalatine/pterygopalatine recess;

(ii) the sheath straightens the intrinsic curvature of the catheter when the catheter hub is positioned in an extended position;

(iii) the catheter is traversed within the sheath when the insertion portion of the catheter hub is advanced into the catheter hub receiving space of the sheath hub from the extended position;

(iv) the sheath is structurally rigid enough to maintain the intrinsic curvature of the catheter in a straightened form until the insertion end of the catheter exits from a distal end portion of the sheath; and (v) an outer diameter of the distal end portion of the sheath is tapered and rotationally symmetric around a longitudinal axis of the sheath such that the distal end portion of the sheath slopes to a vertex, the vertex aligning with a beginning of a curve of a tip of the insertion end of the catheter to form a continuous transition between the vertex and the beginning of the curve when the catheter hub is positioned in the extended position; and an arresting element comprising a flange with a sloped surface extending perpendicularly from a distal end of the insertion portion of the catheter hub, and an engagement element comprising a stopping element with a sloped surface extending perpendicularly from the interior surface defining the catheter hub receiving space, wherein the sloped surface of the stopping element is engaged by the sloped surface of the flange to facilitate insertion of the catheter hub into the catheter hub receiving space, wherein the arresting element continuously engages the engagement element when the catheter hub is received in the catheter hub receiving space and repositioned along a longitudinal axis of the sheath hub, and wherein engagement between the arresting element and the engagement element prevents rotation of the sheath hub with respect to the catheter hub.

2. The apparatus of claim 1, further comprising a rotational orientation indicator, the rotational orientation indicator identifying a rotational orientation of the intrinsic curvature of the catheter.

3. The apparatus of claim 2, wherein the rotational orientation indicator comprises a raised ridge extending longitudinally along at least one of the sheath hub and the catheter hub.

4. The apparatus of claim 1, wherein the catheter hub is positionable between the extended position and an inserted position.

5. The apparatus of claim 1, wherein the tip of the insertion end of the catheter comprises a tip that is curved such that the tip is rounded.

6. The apparatus of claim 5, wherein the transition between the vertex and the beginning of the curve of the rounded tip of the catheter is continuous when the catheter hub is positioned in the extended position.

7. The apparatus of claim 1, wherein the tip of the insertion end of the catheter is bulbous.

8. The apparatus of claim 1, wherein the engagement element further comprises a recess extending longitudinally along the interior surface of the sheath hub, and wherein the flange is positioned within and travels along the recess when the catheter hub is repositioned along the longitudinal axis of the sheath hub.

9. The apparatus of claim 1, wherein the stopping element is configured to engage the arresting element to prevent the catheter hub from being removed from the catheter hub receiving space of the sheath hub.

10. The apparatus of claim 1, wherein the catheter hub comprises at least one depth indicator that indicates a position of the insertion end of the catheter relative to the distal end portion of the sheath.

11. The apparatus of claim 1, wherein the sheath comprises at least one depth indicator that indicates a position of the sheath within a patient's nasal cavity.

12. The apparatus of claim 11, wherein the at least one depth indicator is provided along an exterior surface of the sheath.

* * * * *